(12) United States Patent
Schuurink et al.

(10) Patent No.: US 9,598,473 B2
(45) Date of Patent: Mar. 21, 2017

(54) TRICHOME-SPECIFIC TRANSCRIPTION FACTOR MODULATING TERPENE BIOSYNTHESIS

(75) Inventors: Robert Cornelis Schuurink, Wageningen (NL); Michael Albertus Haring, Wageningen (NL); Eleni Spyropoulou, Wageningen (NL)

(73) Assignee: Keygene N.V., Wageningen (NL)

( * ) Notice: Subject to any disclaimer, the term of this patent is extended or adjusted under 35 U.S.C. 154(b) by 399 days.

(21) Appl. No.: 14/124,629

(22) PCT Filed: Jun. 8, 2012

(86) PCT No.: PCT/NL2012/050403
§ 371 (c)(1),
(2), (4) Date: Mar. 6, 2014

(87) PCT Pub. No.: WO2012/169893
PCT Pub. Date: Dec. 13, 2012

(65) Prior Publication Data
US 2014/0173771 A1    Jun. 19, 2014

Related U.S. Application Data

(60) Provisional application No. 61/495,399, filed on Jun. 10, 2011.

(51) Int. Cl.
| | | |
|---|---|---|
| C07K 14/415 | (2006.01) | |
| A01H 5/12 | (2006.01) | |
| A01H 5/00 | (2006.01) | |
| C12N 15/82 | (2006.01) | |
| A01H 1/02 | (2006.01) | |

(52) U.S. Cl.
CPC ............. *C07K 14/415* (2013.01); *A01H 1/02* (2013.01); *A01H 5/00* (2013.01); *A01H 5/12* (2013.01); *C12N 15/8243* (2013.01); *C12N 15/8286* (2013.01)

(58) Field of Classification Search
None
See application file for complete search history.

(56) References Cited

U.S. PATENT DOCUMENTS

2009/0049566 A1* 2/2009 Zhang ................ C12N 15/8261
800/266

FOREIGN PATENT DOCUMENTS

| WO | WO-93/05163 | 3/1993 |
|---|---|---|
| WO | WO-00/46383 | 8/2000 |
| WO | WO-03/004690 | 1/2003 |
| WO | WO 03/054142 | 7/2003 |
| WO | WO-2004/069849 | 8/2004 |
| WO | WO-2004/070005 | 8/2004 |
| WO | WO-2004/070007 | 8/2004 |
| WO | WO-2005/003375 A2 | 1/2005 |
| WO | WO-2007/037678 A2 | 4/2007 |
| WO | WO-2009/082208 | 7/2009 |
| WO | WO-2010/099985 A2 | 9/2010 |

OTHER PUBLICATIONS

EMBL Database with Accession No. GT170533.1, H_Ea0012N05.r LH_Ea Solanum habrochaites cDNA, published Oct. 19, 2009.*
Besser et al., 2009, Plant Physiology 149: 499-514.*
Solanum habrochaites sequence LH_Ea0012N05.r, with EBI accession No. GT170533, published Oct. 19, 2009.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Tomato Genome Consortium, 2012, Nature 485: 635-641.*
Adams, Identification of Essential Oil Components by Gas Chromatography/Mass Spectrometry, 4th ed., 2007, Allured Pub Corp., Carol Stream, IL. (Table of Contents only).
Aharoni, et al. "Metabolic engineering of terpenoid biosynthesis in plants", Phytochemistry Reviews, 2006, vol. 5, pp. 49-58.
Aharoni, et al. "Terpenoid Metabolism in Wild-Type and Transgenic Arabidopsis Plants",The Plant Cell, Dec. 2003, vol. 15, pp. 2866-2884.
Altschul et al., "Basic Local Alignment Search Tool," J. Mol. Biol., 1990, vol. 215, pp. 403-410.
Antonious, "Production and Quantification of Methyl Ketones in Wild Tomato Accessions", Journal of Environmental Science and Health, Part B: Pesticides, Food Contaminants, and Agricultural Wastes, 2001, vol. 36, No. 6, pp. 835-848.
Antonious, et al. "Natural Products: Seasonal Variation in Trichome Counts and Contents in *Lycopersicum hirsutum f. glabratum*", Journal of Environmental Science and Health, Part B: Pesticides, Food Contaminants, and Agricultureal Wastes, 2005, vol. 40, pp. 619-631.
Arabidopsis—A Laboratory Manual Eds. Weigel and Glazebrook, 2002, Cold Spring Harbor Laboratory Press (Table of Contents only).

(Continued)

*Primary Examiner* — David T Fox
*Assistant Examiner* — Bratislav Stankovic
(74) *Attorney, Agent, or Firm* — Foley & Lardner LLP; Sunit Talapatra

(57) ABSTRACT

The present invention relates to identification and isolation of zinc finger transcription factor in tomato that specifically expresses in glandular trichomes of *Solanum lycopersicum* cultivar Moneymaker and binds to the promoters of the genes encoding Terpene Synthase 5 (also known as Monoterpene Synthase 1) and Terpene Synthase 11 (also known as Sesquiterpene Synthase 1). The invention provides the isolated, recombinant or synthetic polynucleotides encoding the polypeptide sequences of SEQ ID NO:2 and variants and fragments thereof. The invention also provides constructs, vectors, host cells and plants genetically modified to contain the polynucleotides of the invention. The methods for producing plants with altered levels of terpenes, including transformed and mutant plants, are also provided.

14 Claims, 9 Drawing Sheets

(56) References Cited

OTHER PUBLICATIONS

Ausubel, et al., Current Protocols in Molecular Biology, 2000, vol. 2, Wiley & Sons, NY.

Ayvaz, et al. "Insecticidal activity of the essential oils from different plants against three stored-product insects", Journal of Insect Science, 2010, vol. 10, Article 21, pp. 1-13.

Baulcombe, "Amplified Silencing", Science, Jan. 2007, vol. 315, pp. 199-200.

Bevan, et al., "A chimaeric antibiotic resistance gene as a selectable marker for plant cell transformation", Nature, 1983, vol. 304, pp. 184-187.

Bleeker et. al., "Tomato-produced 7-epizingiberene and R-curcumene act as repellents to whiteflies", Phytochemistry, Jan 2011, vol. 72, pp. 68-73.

Bleeker, et al. "The Role of Specific Tomato Volatiles in Tomato-Whitefly Interaction", Plant Physiology, Oct. 2009, vol. 151, pp. 925-935.

Blochlinger, et al. "Hygromycin B Phosphotransferase as a Selectable Marker for DNA Transfer Experiments with Higher Eucaryotic Cells", Molecular and Cellular Biology, Dec. 1984, vol. 4, No. 12, pp. 2929-2931.

Bruce, et al. "Insect host location: a volatile situation", Trends in Plant Science, Jun. 2005, vol. 10, No. 6, pp. 269-274.

Chen, et al. "The family of terpene synthases in plants: a mid-size family of genes for specialized metabolism that is highly diversified throughout the kingdom", The Plant Journal, 2011, vol. 66, pp. 212-229.

Cortina, et al. "Tomato transformation and transgenic plant production", Plant Cell, Tissue and Organ Culture, 2004, vol. 76, pp. 269-275.

De Azevedo, et al. "Zingiberene-mediated resistance to the South American tomato pinworm derived from *Lycopersicon hirsutum var. hirsutum*", Euphytica, 2003, vol. 134, pp. 247-251.

Devereux, et al., "A comprehensive set of sequence analysis programs for the VAX", Nucleic Acid Research, 1984, vol. 12, p. 387.

Dieffenbach, et al., 1995, PCR Primer: A Laboratory Manual, Cold Spring Harbor Laboratory Press (Table of Contents only).

Feng, et al. "Progressive Sequence Alignment as a Prerequisite to Correct Phylogenetic Trees", Journal of Molecular Evolution, 1987, vol. 25, pp. 351-360.

Freitas, et al., "Inheritance of foliar zingiberene contents and their relationship to trichome densities and whitefly resistance in tomatoes", Euphytica, 2002, vol. 127, pp. 275-287.

Frelichowski Jr., et al., "Sesquiterpene Carboxylic Acids form a Wild Tomato Species Affect Larval Feeding Behavior and Survival of Helicoverpa zea and Spodoptera exigua (Lepidoptera: Noctuidae)", J Econ Entomol, Oct. 2001, vol. 94, p. 1249.

Fridman, et al. "Metabolic, Genomic, and Biochemical Analyses of Glandular Trichomes from the Wild Tomato Species *Lycopersicon hirsutum* Identify a Key Enzyme in the Biosynthesis of Methylketones", The Plant Cell, Apr. 2005, vol. 17, pp. 1252-1267.

Gershenzon, et al. "The function of terpene natural products in the natural world", Nat Chem Biol, Jul. 2007, vol. 3, No. 7, pp. 408-414.

Gigolashvili, et al. "HAG2/MYB76 and HAG3/MYB29 exert a specific and coordinated control on the regulation of aliphatic glucosinolate biosynthesis in Arabidopsis thaliana", New Phytologist, 2008, vol. 177, pp. 627-642.

Gigolashvili, et al. "The R2R3-MYB transcription factor HAG1/MYB28 is a regulator of methionine-derived glucosinolate biosynthesis in *Arabidopsis thaliana*", The Plant Journal, 2007, vol. 51, pp. 247-261.

Goffreda, et al. "Chimeric Tomato Plants Show that Aphid Resistance and Triacylglucose Production ARe Epidermal Autonomous Characters", The Plant Cell, Jul. 1990, vol. 2, pp. 643-649.

Goldschmidt-Clermont, "Transgenic expression of aminoglycoside adenine transferase in the chloroplast: a selectable marker for site-directed transformation of chlamydomonas", Nucleic Acids Research, 1991, vol. 19, No. 15, pp. 4083-4089.

Hamilton et al., "A Species of Small Antisense RNA in Post-transcriptional Gene Silencing in Plants", Science, Oct. 29, 1999, vol. 286, pp. 950-952.

Hammond, et al. "Post-Transcriptional Gene Silencing by Double-Stranded RNA", Nature Rev. I Genet., 2001, vol. 2, pp. 110-119.

Hellens, et al. "pGreen: a versatile and flexible binary Ti vector for Agrobacterium-mediated plant transformation", Plant Molecular Biology, 2000, vol. 42, pp. 819-832.

Herde, et al. "Identification and Regulation of TPS04/GES, an *Arabidopsis* Geranyllinalool Synthase Catalyzing the First Step in the Formation of the Insect-Induced Volatile $C_{16}$ -Homoterpene TMTT", Plant Cell, 2008, vol. 20, pp. 1152-1168.

Higgins, et al. "Using Clustal for Multiple Sequence Alignments", Methods in Enzymology, 1996, vol. 266, pp. 383-402.

Hinchee, et al., "Production of Transgenic Soybean Plants Using Agrobacterium-mediated DNA Transfer", Biotechnology, Aug. 1988, vol. 6, pp. 915-922.

Jefferson, et al. "GUS fusions: beta-glucuronidase as a sensitive and versatile gene fusion marker in higher plants", The EMBO Journal, 1987, vol. 6, No. 13, pp. 3901-3907.

Juvik, et al. "Acylglucoses from Wild Tomatoes Alter Behavior and Reduce Growth and Survival of *Helicoverpa zea* and *Spodoptera exigua* (Lepidoptera: Noctuidae)", Journal of Economic Entomology, Apr. 1994, vol. 87, No. 2, pp. 482-492.

Kauffman, et al. "Inhibition of Campoletis sonorensis Parasitism of Heliothis zea and of Parasitoid Development by 2-Tridecanone-Mediated Insect Resistance of Wild Tomato", Journal of Chemical Ecology, 1989, vol. 15, No. 6, pp. 1919-1930.

Kharel, et al. "Molecular analysis of cis-prenyl chain elongating enzymes", Nat. Prod. Rep., 2003, vol. 20, pp. 111-118.

Lee, et al. "The molecular basis of sulfonylurea herbicide resistance in tobacco", The EMBO Journal, 1988, vol. 7, No. 5, pp. 1241-1248.

Lewinsohn, et al. "Enhanced Levels of the Aroma and Flavor Compound S-Linalool by Metabolic Engineering of the Terpenoid Pathway in Tomato Fruits", Plant Physiology, 2001, vol. 127, pp. 1256-1265.

Lucker, et al. "Increased and Altered Fragrance of Tobacco Plants after Metabolic Engineering Using Three Monoterpene Synthases from Lemon", Plant Physiol, 2004, vol. 134, pp. 510-519.

Lucker, et al. "Metabolic engineering of monoterpene biosynthesis: two-step production of (+)-trans-isopiperitenol by tobacco", The Plant Journal, 2004, vol. 39, pp. 135-145.

Maniatis, et al., "Molecular Cloning—A Laboratory Manual", 1982, Cold Spring Harbor Laboratory Press (Table of Contents only).

McPherson, et al., 2000, PCR Basics: From Background to Bench, 1st ed., Springer Verlag, Germany (Table of Contents only).

Myers, et al., "Optimal alignments in linear space", Comput Appl Biosci, 1988, vol. 4, No. 1, p. 11-17.

Navia-Gine, et al. "Medicago truncatula E-(beta)-ocimene synthase is induced by insect herbivory with corresponding increases in emission of volatile ocimene", Plant Physiology and Biochemistry, 2009, vol. 47: 416-425.

Needleman, et al., "A General Method Applicable to the Search for Similarities in the Amino Acid Sequence of Two Proteins", J. Mol. Biol., 1970, vol. 48, p. 443-453.

Sallaud, et al. "A Novel Pathway for Sesquiterpene Biosynthesis from Z,Z-Farnesyl Pyrophosphate in the Wild Tomato *Solanum habrochaites*", The Plant Cell, Jan. 2009, vol. 21, pp. 301-317.

Schilmiller, et al. "Monoterpenes in the glandular trichomes of tomato are synthesized from a neryl diphosphate precursor rather than geranyl diphosphate", PNAS, Jun. 30, 2009, vol. 106, No. 26, pp. 10865-10870.

Seo, et al. "Photocleavable fluorescent nucleotides for DNA sequencing on a chip constructed by site-specific coupling chemistry", PNAS, Apr. 13, 2004, vol. 101, No. 15, pp. 5488-5493.

Spencer, et al. "Bialaphos selection of stable transformants from maize cell cult", Theoretical and Applied Genetics, May 1990, vol. 79, Issue 5, pp. 625-631.

Tholl, "Terpene synthases and the regulation, diversity and biological roles of terpene metabolism", Current Opinion in Plant Biology, 2006, vol. 9, Issue 3, pp. 1-8.

Thompson, et al. "Clustal W: improving the sensitivity of progressive multiple sequence alignment through sequence weighting,

(56) References Cited

OTHER PUBLICATIONS position-specific gap penalties and weight matrix choice", Nucleic Acids Research, 1994, vol. 22, No. 22, pp. 4673-4680.
Van Der Hoeven, et al. "Genetic Control and Evolution of Sesquiterpene Biosynthesis in *Lycopersicon esculentum* and *L. hirsutum*", The Plant Cell, Nov. 2000, vol. 12, pp. 2283-2294.
Van Engelen, et al. "pBINPLUS: an improved plant transformat on vector based on pBIN19", Transgenic Research, 1995, vol. 4, pp. 288-290.
Van Leeuwen, et al., "The Use of the Luciferase Reporter System for in Planta Gene Expression Studies", Plant Molecular Biology Reporter, 2000, vol. 18 pp. 143-143.
Vieira, et al. "The pUC plasmids, an M13mp7-derived system for insertion mutagenesis and sequencing with synthetic universal primers", GENE, 1982, vol. 19, pp. 259-268.
Wang, et al. "Isoprenyl diphosphate synthases", Biochimicia et Biophysica Acta, 2000, vol. 1529, pp. 33-48.
White, et al. "A cassette containing the bar gene of Streptomyces hygroscopicus: a selectable marker for plant transformation", Nucleic Acids Research, Dec. 1989, vol. 18, No. 4, p. 1062.
Williams, et al., "2-Tridecanone: A Naturally Occurring Insecticide from the Wild Tomato *Lycopersicon hirsutum f. glabratum*", Science, Feb. 1980, vol. 207, p. 888-889.
Withers, et al., "Biosynthesis and engineering of isoprenoid small molecules", Applied Microbial Biotechnology, 2007, vol. 73, pp. 980-990.
Xu, et al. "Characterization of GaWRKY1, a Cotton Transcription Factor That Regulates the Sesquiterpene Synthase Gene (+)-δ—Cadinene Synthase-A", Plant Physiology, May 2004, vol. 135, pp. 507-515.
Broun et al., "Importance of transcription factors in the regulation of plant secondary metabolism and their relevance to the control of terpenoid accumulation," Phytochemistry Reviews, vol. 5, No. 1, Jul. 2006, XP019405399, pp. 27-38.
Database accession No. AWH37850, Transcription factor nucleotide sequence, SEQ ID 7647, Jul. 2009, XP002666613, 3 pages.
Database EMBL [Online], "LH_Ea0012N05.r LH_Ea Solanum habrochaites cDNA, mRNA sequence," EBI accession No. GT170533, Oct. 2009, XP002666610, 2 pages.
Gantet et al., "Transcription factors: tools to engineer the production of pharmacologically active plant metabolites,"Trends in Pharmacological Sciences, vol. 23, No. 12, Dec. 2002, XP004394699, pp. 563-569.
Gigolashvili et al., "The transcription factor HIG1/MYB51 regulates indolic glucosinolate biosynthesis in Arabidopsis thaliana," The Plant Journal, vol. 50, 2007, XP002666614, pp. 886-901.
International Search Report for PCT/NL2012/050403 dated Sep. 3, 2012, 3 pages.
McDowell et al., "Comparative Functional Genomic Analysis of Solanum Glandular Trichome Types," Plant Physiology, vol. 155, No. 1, Jan. 2011, XP002666611, pp. 524-539.
Misra et al., "Modulation of Transcriptome and Metabolome of Tobacco by Arabidopsis Transcription Factor, AtMYB12, Leads to Insect Resistance, " Plant Physiology, vol. 152, No. 4, Apr. 2010, XP00266615, pp. 2258-2268.
"Plant transcription factor sequence, SEQ ID 748," accession No. AWH30951, Jul. 2009, XP0266612, 4 pages.
Van Schie et al., "Regulation of terpenoid and benzenoid production in flowers," Current Opinion in Plant Biology, vol. 9, No. 2, Apr. 2006, XP028014923, pp. 203-208.
Van Schie et al., "Tomato linalool synthase is induced in trichomes by jasmonic acid," Plant Molecular Biology, vol. 64, No. 3, Apr. 2007, XP019507419, pp. 251-263.

* cited by examiner

FIGURE 5A

GCAAGTCAAATTGTATATGCTCTTAATTAGGGTTTATGCACCTAGAAGTAGTA
TTTTAATCGCATATTAGTTATCGATGTTCCTAAATTAATCGCCTATTAGTTATC
GATGTTCCTAAATATAATTGACCTAATTACAAAATTAAGATAGAACTGATTAT
ATTTTTTCAATTTTATCCTTACAAGGAGCAATTCTTTTTGAAAGTATGAACCA
CTTTGTAAAGTTTTTTTTAAAAAAAATCTTAAAGGAGTAAATCAGTAAAACT
ACCTTTCATATTTATGATTTTTAAGAAGCATGTAAAGAAAAATAGAAAATC
AATATAGAACGAAAAAGAATTTTATAAAACCTCATAACTTAATAAAAAGAA
TCATATTTATAAGAAATATTTCTTCCCACATGGAATAATAAATTGCACAAAC
TGTAAATATTCTCTACTACAATATAATGTTATAACACACGTATACCGTTGGTT
TTTCAGTATAAATATAATATCCATATTTTAGATATATTAGCTGTTAAAAACAA
TATAATATGGATGGAGACAAGTTAAATGTATGTAATTTTACCTTGTAATCCCA
ATTCTCAATATATATATATATATATATATATATATATTCCTCCAAGACAAA
ACATTGGATTTTTATTCTAGGAACTTGAATTAAGAATTCAATTTACTCGTAAA
AATTAAAAGAAATTTCTTATGATCTTATCAAATATTTAATAGGTGAATAGTT
AAATTTGACAAGTTAAATTAAGATGTATGTCCATCACCTCATCATAATTCAAA
TTATTTTAACAAATATCCTTAATCATGATCTTCTTTCTTTTTAGGTTGAAATAA
TTATCATTAGATTTGTACATAGTATAGGAATATATTAAGAGCTAATATATCTA
AAATGTGGATAAATAAAACAATTCTTGCTCAAAATTTTAAATAGTTTTAATAC
TTTTACAATACTTGACACGCGGCATTATATAGCCAACAATTTTACGGGCTAAG
ACATAACATTTATCTTGGAAATTCTCTATTATTAATCATTAGCTTAGATTGTCT
GAGTTTTTGAAGGTCTTTTATTTAGTTATAGGCAATTTTACCTAGTTTTATAGA
ATTAAAATTATTGTCCGTTGTTATATTTAGGTAAGAAAAAAGTTAATAAATC
AGACAAGAAAATATAAAGAACCGAAATAATTATGTAATGCCTAAAATAGTTG
GTTTTATATACATAAAGACTGTTGAAAATTGAAATTAATATTGCGGCTCCTTC
ATTTATTGGTATTACTGTTAATTACGTGATTGAAAGGAAAAAAAAGTTTTAC
CAAAAAAAGTATAAAAATAAGTTTTGTACTTTATGTCAACAGTTAGTCATC
AATAGTTACTGCTATAATACTAGGTGCCAACACTATGTATAATTCGAATGTGA
TAATAATTTCTGGAAAAAAAATTAAAGGATATTTGATTTGATATGGTCCTAG
ATAATGTAGATGATGAAGGGGTGTTAATTAGTCGTTTCAAATTGATAGGTTAT

FIGURE 5B

TTTGAAAAATTGTGTCATATTAATTGTTTATATTTTCAATGATGTATGATTAAA
ATTAAAATTTTTGAATCTGTCTTAATCGTTTTGGTTTCTCTTTGATTTAGGTAT
AATTCAAATTGATGGTTAATTTTTTAAACGTCATCTAACAACTATAAAATTT
GATAAAAATATTTAAATTTACAATAACATAAATGAAATATGTTTTCCA
ACTATACCAATTTAGGAGGAGAAACATAGTTATTGTTTACTATTATCGCTAG
TATTATGAATGAGATATGAAAATTTATATTAATTTATATTGGAATCTATAATT
GATTTATTAAAAAAATTAAGTGCGTGTACTTTGACATTTTTTTGTTTTAA
CTCGGCATTCAAAGTTCATATTGAAGTTTTAACTAAATTCGAATCGCACTCTT
CAGAGCAATGCAGGGATGGGTCTCCCAACAACATTTTGTCGATAGTCTATAC
CCAGAGCTCGAACTTAAGACCTCTGATTAAGAATAAAATACTTCATTTATAA
ACTGATCATCTTAATATTTTCAAAATTTAAATGTCACATATTTCTAAGATATC
CTCGAAACATAATAATAAGTTGAAATGTATAATGTTTGATTGAGACTAAACT
GAGGCGTTTATATATACAATCGTAGAATTAAAATATTTAATTGCCATCTGAAA
ATTAATTTAAATATTTATCTATGTACTATACCTTAATTAATTCTTTCATGACAA
ACTTTCTTGGACATTTTTTCATGAAAAATGCATATAACTTAAACAAGGCCGAT
ACCTTACACCCAAATTGGACAGTATATTTAGAAGAGGGGGAATAATGGTAAA
GAGGGCCGGTATCAGGTTTACACAGAGATGAAAGTTAGGTGGAGTTTATTT
GTTCGGATGGATTTATCAGTTTTTTCGTAGATTTTATATTTATATTAGATTCTT
TTTTTTACGTATATATTAAATTATAATCCCTAAACAAATTGATTTAGAATCTC
AAACTCATAATCTTAACTTCGCCCCTAACTTTTATATATATATATATATATATA
ATATTTTTAATATATCATTAGTTACACATTATTTTTTATATTATGTTGTGTATT
ACTGATGAATAATGATTTATGGAAATACAAAAAGCTCTTATTCAGTAATACA
TACATTAGTATGATCATCTTTTTTCACATTCTTTCCATCGCGATATATGTTTTT
TTTTTAAACTATAACACAATAAACACTGCATTAAAAATAATTGTACATATTTT
TTGTGTCTCAATTTATGTGATACCTTTTAGTTTTTTAAGAGCTAAACAATTTAA
ATTTGAGCGAGAATTTACGCATGAAATTTTCGAAAATTCTAAAAAGAAATTT
ATATATTAATAAAAACTACGTAAAAATACTATAAGACACAATAATTGACAAT
TCAAAATATTTAAAAGTCAAAGATATACTTATTTGAATTTCAAAATCTGAAAA
GTATCACATAAATAGGAGGAGAGAGTAACGAATATCAATATTAATGATATAT
TATATTCACCACTAATATTCTTAAAAATAAATATTAAAAACACCATTAAATTC
GATGTGAATTATTAGTTTGATCCCTGAACTATTGACAGTATTATAAACACTCC

FIGURE 5C

TCTACTGGGTTAGATGAACTTAAATACACACTCGATCTTGTCACAATGATGAA
ATACACCCTAATGAAAATCATATTTACTCTTCCTATTTCTAACCATCGGAAAG
AGTCATCGTGGCTAGGAAACTATACTAGCGACCTACCCAATTCATTATAGAA
ATTTTCGCGATCAATGATTGAAAATTTAGAATGTTTCCAACACTTTATCTGTC
AACTTTTTATTAAGAGTTTCAAGCTCGTATAAGAATTTGAAATCACTTTTAGT
ATATCATGTAGTAGATCTAAATATATTTAAAATTATTATAAATTTTTTTTAAA
AAACTAATAATTCACACTAAATTGACAAATATCTTCAATACTTAGCTTCTCAC
TTATTTTATACGACCTACCAAACAATCGCGAAACTTTTTAAGTTACTGCAAAC
TGTAGCGGTAAAGAGAGGGGAGGGGGGGGGGGTAGTTGTGGTGCTTTTTAGC
GTTGGCGGCGTTTGCAGAGCTGTAATATATATAATATACCTTTTCTATTAATG
TACCCTCACTCACTCACTTCCTCTCCATAATTCTTTATACAAACAATCATTTTT
TCTTAAACTTGCTCTATTATAAATTCACATTTTTTCTTTATATATACACATACA
TATAGAGCAAAAAAGAAGTTCTAATTTTGTAAACCCTTCAAAAAAAAGAAAA
ATAATTTTTTTGAGATCATAAATGAAGAAATCCAAGGGATACAAACATCAT
ATTTGTGTTATAAGTTGGTGCACTTTTGTGGTATGGATTGTGATTAATCACTA
ATCATAATCAAGATTAACAACAAGTA<u>ATGGCTAATTTCTTTTCATTAGGTGGG
AATCAAGAACAACAACATCAAGAAATTAGCAGCAGCCAAGCATTAGTACCC
ACAGAGAGTAATAATTGGTTTTTGTACAGAAATGAACATCATCATCATCATC
ATAATCAAGAAATACCCAACACTTACAAAGGTTTTGAGTTATGGCAAAGTGG
TAACACTCCACAACACCAACACCAACACCACCAACAACAACAACAGTTTCGT
CATCCGATTTATCCTTTGCAAGATCTTTATTCCACTGATGTTGGATTAGGGGTT
GGGCCAAGCAGAAGTGGCTTTGATATATCTGCAG</u>gtgatcatcagaaacagatttagaatttaaa
ctttatctattcagtactttctaaagtacttatagatctataatttaagtttgataaatttaatatttatgttctaaacaattcacaacattttgc
aattagggatttcgaaacgtatttactgaagcatgttagaattcccagcctcgaaaaggcatgggaatttggtctatggacttggga
aattctccattcatgagctaacttttgaggttaaattaggttcatatgtcatatctttacatgatatcagagtaagattcatctcaattcttt
gttcaccaatattggcccccccatattattgtgtccacaatctagttaacctacgctggcccctccatattacagtgtccacgttctagtt
aacgagatctgggcttgcagaagagtgtaaagaattcagaaaaaggatgagtatttggtctccttgtataaacttgagcaatccttc
cttcatgagctagctagttttggaattaagttagactagatgtcatatctttaatatttatgttctcactgtagaaccatatagcaacga
aactatagtactatttgttgcaccgctctctctatatatatcgtgcatattaagttcaattgaatctgttgctaaaaggcgggatgggga
ttattattgtgcag<u>GTGATCATG AGGCGTCGAG GTCGGGATTC
GTGATGATGAGGAGTGGTGGAGGAGGAATAAGTTGCCAAGATTGTGGGAAC</u>

FIGURE 5D

CAAGCTAAGAAAGATTGTCAACATATGAGGTGTAGGACTTGTTGTAAGAGTA
GAGGGTTTCAGTGTCAAACTCATGTGAAAAGTACTTGGGTTCCAGCAGCTAA
AAGGAGAGAAAGGCAACAACAACTTGCTGCTTTGCAACAACAACAACAAGG
ACATAATAATAATAATAATAATCATAAGAATAAAAGGCAAAGGGAGGATCC
AAGTGCTTCTTCTCTTGTGTCTACTCGTTTGCCTTCAAACACTAATGgtaaagtacttc
atgttttcttacctttcattgctacgtctgttttaatttaaaggtcttagtttgactgaacatgaatataagatgttgaaattgaaaaacgt
agataaatatttaaattgaaacgagggaataatattaattttttttgtatcacacaaagacatagagtcttgagatccatcatgtaaaga
agattaatttgatcattgcctaaatgaattctatataaagtaagtctatagagaaaagagaccctatagtaaattcgtcagcttttctttt
tctatttgtcattctcttcttccatcatcactcttctttttattactctacaaaagattgacaaaaattcgtaatgagatatattcaaattttg
agttaattatgaattttttaattctagttaatagaaagtgtgaataaattatttatatgtattactaacaaaatagcaaaactaaaactttact
tgtacccttgcgcgtgtgtatgcacaatttctttctcttagacctacacatgatatttatctcgaccctaaaaagatcaccattattcttaa
tttcaattttcgtcaatttttttttaagataataactattatttgagtaataatatatgtgacttacccaaaaaactgttagtggagtgagtat
ttgagaaaccaactctctaattcatgtataataattggtgttatcatatattgtcattagtattggaattaacttatatatctattagtaaatg
tacttttgaaataataactattatttgagtaataatatatgttgcttaccaaaaaaataactattagttgagtggctattaactctccaaat
atgtataataattggtgttatcattttcattagtattggaattaacttatatatatagtaaatgcacttgcatttcaaattttttttacctgctttt
ccttttagttcgattaaaataaattgactattttttcaagcaagtgtttattctaaacttttcagatgaaatgtttaaaaaaaccacaagatt
aaatagtgttttgatacatttgacatattttagttttagaccataaaattcaaattgctttactaaatttcgtgtcaagtgatactaggtaa
aaaaaaatatttatttgcaatacattagtccaaataaacctaattttgtattatggaatttcatgtgttatttttagGGTTAGAAG
TGGGAAAATTTCCATCAAAAGTACGTAAAGTGCTGTATTTCAGTGTATTCAAA
TGAGTTCAATTGAGGATGATGAAGATCAATTAGCATATCAAGCTGCTGTGAG
CATTGGTGGACATGTTTTCAAAGGAATTTTATATGATCAAGGTCATGAAAGTC
AGTACAATAACATGGTTGCAGCCGGAGGCGATACGTCTTCCGGTGGTAGTGC
TGGCGGAGTTCAGCACCACCACCATAATTCCGCTGCAGTAGCTACCGCCACC
ACTACAAGTGGTGGCGATGCTACTGCAGCGGGTCCATCGAATTTTCTAGATCC
TTCTTTATTTCCAGCTCCCCTTAGCACTTTTATGGTAGCTGGTACGCAATTTTT
TCCACCTTCAAGATCTCCTTGATCGTCCACATTGATAATATTGAGGTGTCTTT
TTAATTTTTATGTCAAGAGATTTGTTTTTAATTGAAGTATTGATGTTGAATTGA
GTTGTTTACATTAATTCTCTTTGGATTCTACATGAAGTTGTTTTTTTTCTCTAG
TTCCTTATGGTTAATTATTGGTATCATATAGATTTGCTTTTTTATTTCACGTTA
AGATGATAATATAAGATAAGATGATAATATACTTAAATGTATATATGTTTTGG
GTTGAGTCTTACGATTACTTATTATTAGAATTTTTTGTATGTGTATTCGGCTCA

FIGURE 5E

TAATGTGCCAAAAGATAACAAAAGCAAAATTTAAGAGCATTCACATAATATT
ATAAGTTTGTGATGGACTGTAAGTATATTTTAGATTTTTTAATTAGAGTTTTA
AATTTAAACCTAAAAGAAATCGTATTTAAAAAGAGCAGTTTACCCTATAAGT
GATTTTTTTAAGAATAAATATGGATTAGTCGAACCCAATAGTCGGGCAACAG
TTAGAAGCTAAAAAGATTATAATTTTAAGAAAATACTTACTTTATAAAATTG
AGATATTTGGTTAAGTTTTTAGAGGGGGAAAAGAAATGTGCTTTTGAATAAT
AGCATGAATTAATCTTTACAATTAGAAAAAAGAAAATTAAAAATACAAAAA
GTAATTGTGAATTAGGTCAAGCACAAACTAAGGTTCTAAAACTGATTTTAA
AAAAAAACTTTTAAATTAATTAATCAACACAAAATTATTACTCTCCAAAAAT
ATTTTCTACATAATACTTATCAAAATAAATATATTTAGAAAATTTGGCCAAAC
TAACATGACTCTTCTTGATTAAGCACATAAATCAAGTTGTTAATAAAACTTTG
GCTTTATAGCAATGACTCATTTGCTTTCAAAACATAAAAAAATGAACAAACA
TTAAATATATATTTAACGGAGTAAGATATATTCCAAACTAGGACACTAGAAA
TGGTGAAAGCTTAGTACGTTTGGAACATCAATTCAATTAAACTCGAATGTCAC
TGTTTAACTTGTCTTAATATATGTGATAATATTTGATGGATCTTAAATATTATT
TCTTTAAAAAATAATTATTCGTTAGAAGGACAATAAGTGCTACAATGACTTA
AATTTCTAAATTTTCAACTAGGCATAATCCTTCAAAATAACTTTCATCATACT
TTTGAATAATTAAATATGATATTATTGAAGTTATGTAAATTTTCATGTTTCGG
GCTTGTTCGGGTTTTTAAATATCAAATCAAATTATTCGTGTAAAATTTTTAA
AATTATAAATCAGACCAAATTAATAAAATTCAGATTTTTTCGGGGTTTTCAAC
TCTGGGTTGATTCGTATTTTTCAAGTACCAAACCAAACCATTGTGTCGAATTT
TTAAATTTTTAATCAAACCAAACTAATAAACTTCGGATTTTTCCAGATTTTTA
GATTTTTCGGGTAAAGTTTGCATACAAACATATAATTAACTTGTGCTCCAAAT
ATTTCTTTAGTCCAACCATAATATAATTATCTAAGGTATTTCTTGAAAAAATT
ACACAAAAGATGAGATGAGTATTGATGACACAAAAATATTCAATAAAAAAT
AACAATAAATCATCATATAAAATAAATATTGTAAAGTCATAATGAAAATAAT
CATAATTTAAAATTTTTAAATCATGCTAAAATAAGTTTAATAAGTATTAGTTA
CATTATTAAATATTTAAGGAAAACAAAAATTAGATTATGTAAATAAATATAA
AACTAAAGAACAAATATTCAATATTATTGTCATTTTTAGTGTTGAATTGATTT
TTTCTTTTTGCATTAGTATTAATTTAATTTTAATTTAAGCTTTATTATAATTATC
AATCTATGAACTATAATCTATATTGGACCATTCCAAATTCTATATTTTAAACT

FIGURE 5F

TGAAACAATATATTAAAAGTTAAAAACTATGAAATAGTATAAGAAATATTTT
AAAATAATATCAACGTAAATATTTTATGTATAAAATAATATTTTACACATATA
ATATAAGGATTTTTTTCCCGATTTGATTCAATT

SEQUENCE LISTING

```
<160> NUMBER OF SEQ ID NOS: 24

<210> SEQ ID NO 1
<211> LENGTH: 1056
<212> TYPE: DNA
<213> ORGANISM: Lycopersicon esculentum

<400> SEQUENCE: 1
atggctaatt tcttttcatt aggtgggaat caagaacaac aacatcaaga aattagcagc      60
agccaagcat tagtacccac agagagtaat aattggtttt tgtacagaaa tgaacatcat     120
catcatcatc ataatcaaga aatacccaac acttacaaag gttttgagtt atggcaaagt     180
ggtaacactc cacaacacca acaccaacac caccaacaac aacaacagtt tcgtcatccg     240
atttatcctt tgcaagatct ttattccact gatgttggat tagggggttgg gccaagcaga     300 agtggctttg atatatctgc aggtgatcat gaggcgtcga ggtcgggatt cgtgatgatg     360
aggagtggtg gaggaggaat aagttgccaa gattgtggga accaagctaa gaaagattgt     420
caacatatga ggtgtaggac ttgttgtaag agtagagggt ttcagtgtca aactcatgtg     480
aaaagtactt gggttccagc agctaaaagg agagaaaggc aacaacaact tgctgctttg     540
caacaacaac aacaaggaca taataataat aataataatc ataagaataa aaggcaaagg     600
gaggatccaa gtgcttcttc tcttgtgtct actcgtttgc cttcaaacac taatgggtta     660
gaagtgggaa aatttccatc aaaagtacgt acaagtgctg tatttcagtg tattcaaatg     720
agttcaattg aggatgatga agatcaatta gcatatcaag ctgctgtgag cattggtgga     780
catgttttca aaggaatttt atatgatcaa ggtcatgaaa gtcagtacaa taacatggtt     840
gcagccggag gcgatacgtc ttccggtggt agtgctggcg gagttcagca ccaccaccat     900
aattccgctg cagtagctac cgccaccact acaagtggtg gcgatgctac tgcagcgggt     960
ccatcgaatt ttctagatcc ttcttttattt ccagctcccc ttagcacttt tatggtagct    1020
ggtacgcaat ttttccacc ttcaagatct ccttga                              1056

<210> SEQ ID NO 2
<211> LENGTH: 351
<212> TYPE: PRT
<213> ORGANISM: Lycopersicon esculentum

<400> SEQUENCE: 2

Met Ala Asn Phe Phe Ser Leu Gly Gly Asn Gln Glu Gln Gln His Gln
1               5                   10                  15

Glu Ile Ser Ser Ser Gln Ala Leu Val Pro Thr Glu Ser Asn Asn Trp
            20                  25                  30

Phe Leu Tyr Arg Asn Glu His His His His His Asn Gln Glu Ile
        35                  40                  45

Pro Asn Thr Tyr Lys Gly Phe Glu Leu Trp Gln Ser Gly Asn Thr Pro
    50                  55                  60
```

Gln His Gln His Gln His Gln Gln Gln Gln Gln Phe Arg His Pro
65                  70                  75                  80

Ile Tyr Pro Leu Gln Asp Leu Tyr Ser Thr Asp Val Gly Leu Gly Val
            85                  90                  95

Gly Pro Ser Arg Ser Gly Phe Asp Ile Ser Ala Gly Asp His Glu Ala
                100                 105                 110

Ser Arg Ser Gly Phe Val Met Met Arg Ser Gly Gly Gly Ile Ser
        115                 120                 125

Cys Gln Asp Cys Gly Asn Gln Ala Lys Lys Asp Cys Gln His Met Arg
    130                 135                 140

Cys Arg Thr Cys Lys Ser Arg Gly Phe Gln Cys Gln Thr His Val
145             150                 155                 160

Lys Ser Thr Trp Val Pro Ala Ala Lys Arg Arg Glu Arg Gln Gln Gln
                165                 170                 175

Leu Ala Ala Leu Gln Gln Gln Gln Gly His Asn Asn Asn Asn Asn
            180                 185                 190

Asn His Lys Asn Lys Arg Gln Arg Glu Asp Pro Ser Ala Ser Ser Leu
        195                 200                 205

Val Ser Thr Arg Leu Pro Ser Asn Thr Asn Gly Leu Glu Val Gly Lys
    210                 215                 220

Phe Pro Ser Lys Val Arg Thr Ser Ala Val Phe Gln Cys Ile Gln Met
225                 230                 235                 240

Ser Ser Ile Glu Asp Asp Glu Asp Gln Leu Ala Tyr Gln Ala Ala Val
            245                 250                 255

Ser Ile Gly Gly His Val Phe Lys Gly Ile Leu Tyr Asp Gln Gly His
        260                 265                 270

Glu Ser Gln Tyr Asn Asn Met Val Ala Ala Gly Gly Asp Thr Ser Ser
    275                 280                 285

Gly Gly Ser Ala Gly Gly Val Gln His His His Asn Ser Ala Ala
        290                 295                 300

Val Ala Thr Ala Thr Thr Thr Ser Gly Gly Asp Ala Thr Ala Ala Gly
305                 310                 315                 320

Pro Ser Asn Phe Leu Asp Pro Ser Leu Phe Pro Ala Pro Leu Ser Thr
            325                 330                 335

Phe Met Val Ala Gly Thr Gln Phe Phe Pro Pro Ser Arg Ser Pro
        340                 345                 350

<210> SEQ ID NO 3
<211> LENGTH: 9013
<212> TYPE: DNA
<213> ORGANISM: Lycopersicon esculentum

<400> SEQUENCE: 3
gcaagtcaaa ttgtatatgc tcttaattag ggtttatgca cctagaagta gtattttaat    60
cgcatattag ttatcgatgt tcctaaatta atcgcctatt agttatcgat gttcctaaat   120
ataattgacc taattacaaa attaagatag aactgattat attttttcaa ttttatcctt   180
acaaggagca attcttttg aaagtatgaa ccactttgta agtttttttt ttaaaaaaaa   240
tcttaaagga gtaaatcagt aaaactacct ttcatattta tgattttta agaagcatgt   300 aagaaaaaa tagaaaatca atatagaacg aaaaagaat tttataaaac ctcataactt   360 aataaaaga atcatattta taagaaatat tttcttccca catggaataa taaattgcac   420
aaactgtaaa tattctctac tacaatataa tgttataaca cacgtatacc gttggttttt   480
cagtataaat ataatatcca tattttagat atattagctg ttaaaaacaa tataaatatgg   540

```
atggagacaa gttaaatgta tgtaatttta ccttgtaatc ccaattctca atatatatat    600
atatatatat atatatatat attcctccaa gacaaaacat tggattttta ttctaggaac    660
ttgaattaag aattcaattt actcgtaaaa attaaaaaga aatttcttat gatcttatca    720
aatatttaat aggtgaatag ttaaatttga caagttaaat taagatgtat gtccatcacc    780
tcatcataat tcaaattatt ttaacaaata tccttaatca tgatcttctt tcttttttagg   840 ttgaaataat tatcattaga tttgtacata gtataggaat atattaagag ctaatatatc    900
taaaatgtgg ataaataaaa caattcttgc tcaaattttt aaatagtttt aatactttta    960
caatacttga cacgcggcat tatatagcca acaattttac gggctaagac ataacattta   1020
tcttggaaat tctctattat taatcattag cttagattgt ctgagttttt gaaggtcttt   1080
tatttagtta taggcaattt tacctagttt tatagaatta aaattattgt ccgttgttat   1140
atttaggtaa gaaaaaaagt taataaatca gacaagaaaa tataaagaac cgaaataatt   1200
atgtaatgcc taaaatagtt ggttttatat acataaagac tgttgaaaat tgaaattaat   1260
attgcggctc cttcatttat tggtattact gttaattacg tgattgaaag gaaaaaaaaa   1320
gttttaccaa aaaaagtat aaaaataagt tttgtacttt atgtcaacag ttagtcatca   1380
atagttactg ctataatact aggtgccaac actatgtata attcgaatgt gataataatt   1440
tctggaaaaa aaaattaaag gatatttgat ttgatatggt cctagataat gtagatgatg   1500 aagggggtgtt aattagtcgt ttcaaattga taggttattt tgaaaaattg tgtcatatta   1560
attgtttata ttttcaatga tgtatgatta aaattaaaat ttttgaatct gtcttaatcg   1620
ttttggtttc tctттtgattт aggtataatt caaattgatg gттaattтттt ttaaacgtca   1680 tctaacaact ataaaatttg ataaaaaaata tttaaaattt acaataacat aaaatgaaaa   1740 tatgтттттсс aactatacca atttaggagg agaaacatag ttattgtttt actattatcg   1800
ctagtattat gaatgagata tgaaaattta tattaattta tattggaatc tataattgat   1860

ттттattaaaa aaaattaagt gcgtgtactt tgacattttt tttgttttta actcggcatt   1920
caaagttcat attgaagttt taactaaaттт cgaatcgcac tcttcagagc aatgcaggga   1980
tgggtctccc aacaacattt tgtcgatagt ctatacccag agctcgaact taagacctct   2040
gattaagaat aaaatacttc aттттaтaaac tgatcatctt aaтaтттттсa aaaттттaaaт   2100 gtcacatatt тттcтaagaтa tcctcgaaac ataataataa gтттgaaaтgт ataatgtttg   2160 attgagacta aactgaggcg tttatatata caatcgtaga attaaaatat ttaattgcca   2220

tctgaaaatt aatttaaata tttatctatg tactatacct taattaattc ттттcaтgaca   2280 aactttcttg gacattttt catgaaaaat gcatataact taaacaaggc cgatacctta   2340
cacccaaatt ggacagtata tttagaagag gggataat ggtaaagagg gccggtatca   2400
ggtttacaca gagatgaaaa gttaggtgga gtttatttgt tcggatggat tatcagttt   2460

ттттcgтagaт tttatattta таттagaтттc тттттттттac gtatatatta attataatc   2520 cctaaacaaa ttgatttaga atctcaaact cataatctta acttcgcccc taactttaat   2580

атататат ататаата тт тттааат атат cатт aд тта cа catt a ттттттатат   2640

tatgttgtgt attactgatg aataatgatt tatggaaata caaaaagctc ttattcagta   2700
atacatacat tagtatgatc aтcтттттттс acattctttc catcgcgata tatgttttt   2760

ttttaaacta taacacaata aacactgcat таааааатаат tgtacatat т тттгтгтgтcт   2820 caattttatgt gataccttt agтттттттaa gagctaaaca aттттaaaттт gagcgagaat   2880
```

```
ttacgcatga aattttcgaa aattctaaaa agaaatttat atattaataa aaactacgta    2940
aaaatactat aagacacaat aattgacaat tcaaaatatt taaaagtcaa agatatactt    3000
atttgaattt caaaatctga aaagtatcac ataaatagga ggagagagta acgaatatca    3060
atattaatga tatattatat tcaccactaa tattcttaaa aataaatatt aaaaacacca    3120
ttaaattcga tgtgaattat tagtttgatc cctgaactat tgacagtatt ataaacactc    3180
ctctactggg ttagatgaac ttaaatacac actcgatctt gtcacaatga tgaaatacac    3240
cctaatgaaa atcatattta ctcttcctat ttctaaccat cggaaagagt catcgtggct    3300
aggaaactat actagcgacc tacccaattc attatagaaa ttttcgcgat caatgattga    3360
aaatttagaa tgtttccaac actttatctg tcaactttt  attaagagtt tcaagctcgt    3420
ataagaattt gaaatcactt ttagtatatc atgtagtaga tctaaatata tttaaaatta    3480
ttataaattt ttttaaaaa  actaataatt cacactaaat tgacaaatat cttcaatact    3540
tagcttctca cttattttat acgacctacc aaacaatcgc gaaactttt  aagttactgc    3600
aaactgtagc ggtaaagaga ggggagggg  gggggtagt  tgtggtgctt tttagcgttg    3660
gcggcgtttg cagagctgta atatatataa tatacctttt ctattaatgt accctcactc    3720
actcacttcc tctccataat tctttataca aacaatcatt ttttcttaaa cttgctctat    3780
tataaattca cattttttct ttatatatac acatacatat agagcaaaaa agaagttcta    3840
attttgtaaa cccttcaaaa aaagaaaaa  taattttttt tgagatcata aatgaagaaa    3900
tccaagggat acaaacatca tatttgtgtt ataagttggt gcactttgt  ggtatggatt    3960
gtgattaatc actaatcata atcaagatta acaacaagta atggctaatt tcttttcatt    4020
aggtgggaat caagaacaac aacatcaaga aattagcagc agccaagcat tagtacccac    4080
agagagtaat aattggtttt tgtacagaaa tgaacatcat catcatcatc ataatcaaga    4140
aatacccaac acttacaaag gttttgagtt atggcaaagt ggtaacactc cacaacacca    4200
acaccaacac caccaacaac aacaacagtt tcgtcatccg atttatcctt tgcaagatct    4260
ttattccact gatgttggat taggggttgg gccaagcaga agtggctttg atatatctgc    4320
aggtgatcat cagaaacaga tttagaattt aaactttatc tattcagtac tttctaaagt    4380
acttatagat ctataatttta gtttgataa atttaatatt tatgttctaa acaattcaca    4440
acattttgca attagggatt tcgaaacgta tttactgaag catgttagaa ttcccagcct    4500
cgaaaaggca tgggaatttg gtctatggac ttgggaaatt ctccattcat gagctaactt    4560
ttgaggttaa attaggttca tatgtcatat ctttacatga tatcagagta agattcatct    4620
caattctttg ttcaccaata ttggccccccc atattattgt gtccacaatc tagttaacct    4680
acgctggccc ctccatatta cagtgtccac gttctagtta acgagatctg gcttgcaga    4740
agagtgtaaa gaattcagaa aaaggatgag tatttggtct ccttgtataa acttgagcaa    4800
tccttccttc atgagctagc tagttttgga attaagttag actagatgtc atatctttta    4860
atatttatgt tctcactgta gaaccatata gcaacgaaac tatagtacta tttgttgcac    4920
cgctctctct atatatatcg tgcatattaa gttcaattga atctgttgct aaaaggcggg    4980
atggggatta ttattgtgca ggtgatcatg aggcgtcgag gtcgggattc gtgatgatga    5040
ggagtggtgg aggaggaata agttgccaag attgtgggaa ccaagctaag aaagattgtc    5100
aacatatgag gtgtaggact tgttgtaaga gtagagggtt tcagtgtcaa actcatgtga    5160
aaagtacttg ggttccagca gctaaaagga gagaaaggca caacaacctt gctgctttgc    5220
aacaacaaca acaaggacat aataataata ataataatca taagaataaa aggcaaaggg    5280
```

```
aggatccaag tgcttcttct cttgtgtcta ctcgtttgcc ttcaaacact aatggtaaag    5340
tacttcatgt ttttcttacc ttttcattgc tacgtctgtt ttaatttaaa ggtcttagtt    5400
tgactgaaca tgaatataag atgttgaaat tgaaaaacgt agataaatat ttaaattgaa    5460
acgagggaat aatattaatt ttttttgtat cacacaaaga catagagtct tgagatccat    5520
catgtaaaga agattaattt gatcattgcc taaatgaatt ctatataaag taagtctata    5580
gagaaaagag accctatagt aaattcgtca gcttttctt tttctatttg tcattctctt    5640
cttccatcat cactcttctt ttttattact ctacaaaaga ttgacaaaaa ttcgtaatga    5700
gatatattca aattttgag ttaattatga atttttaatt ctagttaata gaaagtgtga    5760
ataaattatt tatatgtatt actaacaaaa tagcaaaact aaaactttac ttgtaccctt    5820
gcgcgtgtgt atgcacaatt tctttctctt agacctacac atgatattta tctcgaccct    5880
aaaaagatca ccattattct taatttcaat tttcgtcaat ttttttttaa gataataact    5940
attatttgag taataatata tgtgacttac ccaaaaaact gttagtggag tgagtatttg    6000
agaaaccaac tctctaattc atgtataata attggtgtta tcatatattg tcattagtat    6060
tggaattaac ttatatatct attagtaaat gtacttttga aataataact attatttgag    6120
taataatata tgttgcttac caaaaaaata actattagtt gagtggctat taactctcca    6180
aatatgtata ataattggtg ttatcatttt cattagtatt ggaattaact tatatatata    6240
gtaaatgcac ttgcatttca aatttttta cctgctttc cttttagttc gattaaaata    6300
aattgactat ttttcaagca agtgtttatt ctaaactttt cagatgaaat gtttaaaaaa    6360
accacaagat taaatagtgt tttgatacat ttgacatatt tttagtttta gaccataaaa    6420
ttcaaattgc tttactaaat ttcgtgtcaa gtgatactag gtaaaaaaaa atatttattt    6480
gcaatacatt agtccaaata aacctaattt tgtattatgg aatttcatgt gttatttta    6540 gggttagaag tgggaaaatt tccatcaaaa gtacgtaaag tgctgtattt cagtgtattc    6600
aaatgagttc aattgaggat gatgaagatc aattagcata tcaagctgct gtgagcattg    6660
gtggacatgt tttcaaagga attttatatg atcaaggtca tgaaagtcag tacaataaca    6720
tggttgcagc cggaggcgat acgtcttccg gtggtagtgc tggcggagtt cagcaccacc    6780
accataattc cgctgcagta gctaccgcca ccactacaag tggtggcgat gctactgcag    6840
cgggtccatc gaattttcta gatccttctt tatttccagc tccccttagc acttttatgg    6900
tagctggtac gcaatttttt ccaccttcaa gatctccttg atcgtccaca ttgataatat    6960
tgaggtgtct ttttaattt tatgtcaaga gatttgtttt taattgaagt attgatgttg    7020
aattgagttg tttacattaa ttctctttgg attctacatg aagttgtttt tttttctcta    7080
gttccttatg gttaattatt ggtatcatat agatttgctt ttttatttca cgttaagatg    7140
ataatataag ataagatgat aatatactta aatgtatata tgttttgggt tgagtcttac    7200
gattacttat tattagaatt ttttgtatgt gtattcggct cataatgtgc caaaagataa    7260
caaaagcaaa atttaagagc attcacataa tattataagt ttgtgatgga ctgtaagtat    7320
attttagatt ttttaattag agttttttaaa tttaaaccta aaagaaatcg tatttaaaaa    7380
gagcagttta ccctataagt gatttttta agaataaata tggattagtc gaacccaata    7440
gtcgggcaac agttagaagc taaaaaagat tataatttta agaaaatact tactttataa    7500
aattgagata tttggttaag ttttagagg gggaaaagaa atgtgctttt gaataatagc    7560
atgaattaat ctttacaatt agaaaaaag aaaattaaaa atacaaaaag taattgtgaa    7620
```

```
attaggtcaa gcacaaacta aggttctaaa actgatttta aaaaaaaact tttaaattaa    7680
ttaatcaaca caaattatt actctccaaa aatattttct acataatact tatcaaaata     7740
aatatattta gaaaatttgg ccaaactaac atgactcttc ttgattaagc acataaatca    7800
agttgttaat aaaactttgg ctttatagca atgactcatt tgctttcaaa acataaaaaa    7860
atgaacaaac attaaatata tatttaacgg agtaagatat attccaaact aggacactag    7920
aaatggtgaa agcttagtac gtttggaaca tcaattcaat taaactcgaa tgtcactgtt    7980
taacttgtct aatatatgt gataatattt gatggatctt aaatattatt tctttaaaaa      8040
ataattattc gttagaagga caataagtgc tacaatgact taaatttcta aattttcaac    8100
taggcataat ccttcaaaat aactttcatc atactttga ataattaaat atgatattat      8160
tgaagttatg taaattttca tgtttcgggc ttgttcgggt tttttaaata tcaaatcaaa    8220
ttattcgtgt aaaattttta aaattataaa tcagaccaaa ttaataaaat tcagattttt    8280
tcggggtttt caactctggg ttgattcgta tttttcaagt accaaaccaa accattgtgt   8340
cgaattttta aattttaat caaaccaaac taataaactt cggattttc cagattttta       8400 gattttttcgg gtaaagtttg catacaaaca tataattaac ttgtgctcca aatatttctt     8460
tagtccaacc ataatataat tatctaaggt atttcttgaa aaaattacac aaaagatgag   8520
atgagtattg atgacacaaa atattcaat aaaaaataac aataaatcat catataaaat      8580
aaatattgta aagtcataat gaaaataatc ataatttaaa attttaaat catgctaaaa      8640 taagtttaat aagtattagt tacattatta aatatttaag gaaaacaaaa attagattat    8700
gtaaataaat ataaaactaa agaacaaata ttcaatatta ttgtcatttt tagtgttgaa    8760 ttgattttt cttttgcat tagtattaat ttaattttaa tttaagcttt attataatta        8820
tcaatctatg aactataatc tatattggac cattccaaat tctatatttt aaacttgaaa    8880
caatatatta aaagttaaaa actatgaaat agtataagaa atattttaaa ataatatcaa    8940
cgtaaatatt ttatgtataa aataatattt tacacatata atataaggat ttttttcccg    9000
atttgattca att                                                       9013

<210> SEQ ID NO 4
<211> LENGTH: 26
<212> TYPE: DNA
<213> ORGANISM: Artificial sequence
<220> FEATURE:
<223> OTHER INFORMATION: Primer

<400> SEQUENCE: 4
gctctagatt tatttgttct gctcaa                                            26

<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5
cgagctcgtt tcattcaaag tagtgg                                            26

<210> SEQ ID NO 6
<211> LENGTH: 25
<212> TYPE: DNA
<213> ORGANISM: Artificial Sequence
<220> FEATURE:
<223> OTHER INFORMATION: Primer
```

```
<400> SEQUENCE: 6
cgagctcagc tgaaccaaat cccaa                                        25

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
cgagctcgtc ctattttcc atattg                                        26

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
cgagctcatc aacagtatta aatgtgcttc                                   30

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cgagctcagt aataatgaaa atcgcatcg                                    29

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
cgagctcaca tgtgctattt ttatgcta                                     28

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccaccaacgc tgatcaattc                                              20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
atgtgctgca aggcgattaa g                                            21

<210> SEQ ID NO 13
```

```
<211> LENGTH: 29
<212> TYPE: DNA
<213> ORGANISM: Artificial Sequence
<220> FEATURE:
<223> OTHER INFORMATION: Primer

<400> SEQUENCE: 13
cggaattcac atgtgctatt tttatgcta                                    29

<210> SEQ ID NO 14
<211> LENGTH: 20
<212> TYPE: DNA
<213> ORGANISM: Artificial Sequence
<220> FEATURE:
<223> OTHER INFORMATION: Priemr

<400> SEQUENCE: 14
taataccact acaatggatg                                              20

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
caactgtgca tcgtgcac                                                18

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
ttatggcaaa gtggtaaca                                               19

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
tcagtgtcaa actcatgtg                                               19

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
aagtacgtac aagtgctg                                                18

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
```

```
ttagcaccttt ccagcagatg t                                          21

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
aacagacagg acactcgcac t                                           21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
tacaagtggt ggcgatgcta c                                           21

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
acctcaatat tatcaatgtg gacaatc                                     27

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
catgccatgg ctaatttctt ttcattagg                                   29

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24
cgagctctca aggagatctt gaaggtg                                     27
```

TRICHOME-SPECIFIC TRANSCRIPTION FACTOR MODULATING TERPENE BIOSYNTHESIS

CROSS-REFERENCE TO RELATED APPLICATIONS

This application is the National Phase of International Application No. PCT/NL2012/050403 filed Jun. 8, 2012, published as WO 2012/169893, which claims benefit of priority of U.S. Provisional Application 61/495,399, filed Jun. 10, 2011. The contents of these applications are herein incorporated by reference in their entirety.

FIELD OF THE INVENTION

The present invention relates to a zinc finger transcription factor that regulates terpene biosynthesis in plants, a nucleic acid molecule that encodes the transcription factor and methods of use of the transcription factor for producing plants with altered terpene content.

BACKGROUND OF THE INVENTION

Terpenes constitute a large group of structurally diverse molecules synthesized naturally by organisms as diverse as bacteria, fungi, plants and animals. Much research has been concentrated on the biochemistry and biological functions of terpenes or their derivatives for potential commercial exploitation (Gershenzon and Dudareva 2007 Nat Chem Biol 3:408).

The result of these studies is a variety of terpene-based products ranging from pharmaceuticals, such as anti-cancer drug paclitaxel and anti-malaria drug artemisin, to fragrances and aroma ingredients, such as menthol and patchuol.

In the field of plant breeding, there is an interest in terpene secondary metabolites produced by many plant species to resist pathogens, to repel or kill pests or to attract beneficial organisms, e.g., predators or parasitoids of pest insects or plant pollinators, or other organisms. Wild plant species frequently produce beneficial secondary metabolites lacking in their cultivated relatives, and therefore are an important source of traits for introgression into cultivated varieties. It is known that secondary metabolites, such as volatile terpenoid compounds, can directly influence insect behavior (Bruce et al., 2005 Trends Plant Sci 10:269-274). For instance, methyl ketones and sesquiterpene carboxylic acids identified in *Solanum habrochaites* and acyl-glucose esters from *Solanum pennellii* were found to be toxic to different insect classes, such as Lepidoptera, mites, and aphids (Williams et al., 1980 Science 20:888; Goffreda et al., 1990 Plant Cell 2:643; Juvik et al., 1994 J Econ Entomol 87:482; Frelichowski and Juvik, 2001 J Econ Entomol 94:1249). Often mono- and sesquiterpene hydrocarbons, sesquiterpene acids, methylketones and sugar esters are accumulated in plants in specialized organs such as glandular trichomes on stems and leaves. Several studies correlated the density of glandular trichomes with levels of resistance to pest insects, e.g., maize earworm *Heliothis zea* and Colorado potato beetle (Kauffman and Kennedy, 1989 J Chem Ecol 15:1919-1930; Antonius et al., 2001 J Environ Sci Health B 36:835-848; Antonius et al., 2005 J Environ Sci Health B 40:619-631). The methylketones 2-undecanone and 2-tridecanone accumulated in glandular trichomes of *S. habrochaites* were shown to be toxic to larvae of Colorado potato beetle and adult whiteflies *B. tabaci*, respectively (Antonius et al., 2005 J Environ Sci Health B 40:619-631). The myrtle oil, including the monoterpene linalool among its essential components, was shown to have an insecticidal effect on bean weevils, *Acanthoscelides obtectus* Say (*Coleoptera: Bruchidae*) (Ayvaz et al., 2010 J Insect Sci 10: 1536-2442). The sesquiterpenes zingiberene and curcumene, and the monoterpenes p-cymene, α-terpinene, and α-phellandrene from wild tomato *S. habrochaites* and *S. pennellii*, respectively, were shown to have insecticidal properties (Bleeker et al., 2009 Plant Physiol. 151:925). Bio-assays have demonstrated that the sesquiterpenes 7-epizingiberene and its derivative R-curcumene repelled adult whiteflies from landing on tomato plants (Bleeker et al., 2011 Phytochemistry 72:68), and that plants with endogenous production of zingiberene showed resistance to *Tuta absoluta*. (De Azavedo et al., 2003 Euphitica 134:247-251).

Genetic inheritance of the genes associated with development of different types of glandular trichomes and production of zingiberene was studied in interspecific crosses between *S. lycopersicum*, a cultivated tomato which does not produce zingiberene, and *S. habrochaites*, a wild species with high zingiberene production. In F2 plants from these crosses, zingiberene content correlated with resistance to *B. tabaci*. This study suggested feasibility of breeding plants with high levels of zingiberene, 2-tridecanone, and/or acylsugars, which would lead to high levels of resistance to whiteflies (Freitas et al., 2002 Euphytica 127: 275-287). However, programs on introgression of useful traits into cultivated varieties are time consuming and costly, therefore production of secondary metabolites in plants lacking them or elevating levels of these metabolites in plants synthesizing them—albeit in insufficient levels—is an attractive goal.

The biosynthesis of terpenes in plants has been extensively studied and many genes coding for the pathways steps from precursors to final products were discovered (Wither and Keeling, 2007 Agro Microbial Biotechnology 73:980-990; Sallaud et al., 2009 Plant Cell 31:301).

Due to the widespread infestation of crop and ornamental plant species with pest insects such as *B. tabaci* and the greenhouse whitefly *Trialeurodes vaporarium*, resulting in great economic losses, means of regulating plant natural defense molecules to repel pests has received a renewed interest of scientists and plant breeders.

It is known that manipulation of transcription factors can regulate complex pathways in animals and plants involving numerous target genes. This may result in increased expression of useful compounds. Alternatively, blocking transcription factors may lead to decreased or completely suppressed production of undesirable compounds and/or removal of unwanted traits.

Several transcription factors controlling genes involved in plant secondary metabolism were identified, cloned and showed high efficiency in regulating complex metabolic pathways. For instance, the transcription factor WRKY was shown to regulate δ-Cadenine Synthase A, a sesquiterpene synthase that catalyzes the first step of pathway leading to production of gossypol in cotton (Xu et al., 2004 Plant Physiol 135:507-515).

Moreover, while overexpression of individual genes of the biosynthetic pathways was shown to provide limited success, perhaps, due to poor substrate availability, genome-wide expression of the flavonol-specific transcription factor, AtMYB12, in tobacco not only regulated the phenylpropanoid pathway, but also modulated other metabolic pathways that led to increased flux availability to this pathway, and eventually to an increased resistance against *Spodopter*

*lituralis* and *Helicoverpa armigera* insects (Misra et al., 2010 Plant Physiol 152: 2258-2268).

MYB transcription factors have been indicated also to activate multiple enzymes required for production of glucosinolates, crucifer-specific secondary metabolites, in *Arabidopsis*. MYB51 was shown to activate the indolic glucosinolates biosynthesis and confer enhanced resistance to the herbivorous pest *Spodoptera exigua* in plants overexpressing it (Gigolashvili et al., 2007 Plant J 50: 886-901). Other MYB transcription factors, such as MYB76, MYB28 and MYB29, are shown to regulate enzymes involved in the production of aliphatic glucosinolates (Gigolashvili et al., 2007 Plant J 51: 247-261; Gigolashvili et al., 2008 New Phytol 177:627-642).

There is a need in the art to provide transcription factors regulating terpene biosynthesis, in particular transcription factors that have an effect on the biosynthesis of mono- or sesquiterpenes in plants or other organisms leading to the production of terpene compounds that repel or attract insects, or other organisms.

SUMMARY OF THE INVENTION

An embodiment of the invention herein provides an isolated, synthetic or recombinant nucleic acid sequence selected from the group including: a) a nucleic acid sequence of SEQ ID NO: 1; b) a nucleic acid sequence that encodes a polypeptide having an amino acid sequence of SEQ ID NO: 2 or an amino acid sequence that is at least 60% identical to the amino acid sequence of SEQ ID NO:2; c) a nucleic acid sequence that is at least 60% identical to the nucleic acid sequences of (a) or (b), and encodes a transcription factor that regulates terpene biosynthesis; d) a nucleic acid sequence encoding a polypeptide comprising which has been derived, by way of one or more amino acid substitutions, deletions or insertions, from the polypeptide having the amino acid sequence of SEQ ID NO: 2 and which polypeptide is functionally equivalent to the polypeptide consisting of the amino acid sequence of SEQ ID NO: 2; e) a nucleic acid sequence that hybridizes under stringent conditions to the nucleic acid sequences of (a), (b), (c), or (d); and f) a nucleic acid sequence that hybridizes under stringent conditions to the (optionally reverse) complement of the nucleic acid sequences of (a), (b), (c), or (d) and that encodes the transcription factor that regulates terpene biosynthesis. Further embodiments include a chimeric gene comprising such nucleic acid sequence, a vector comprising such nucleic acid sequence or such chimeric gene, and a host cell comprising such chimeric gene or such vector.

A related embodiment of the invention provides a polypeptide with DNA binding activity that regulates terpene biosynthesis in a plant, such polypeptide having an amino acid sequence selected from the group of: (a) an amino acid sequence of SEQ ID NO: 2; (b) the amino acid sequence according to (a) in which at least one amino acid is substituted, deleted, inserted or added and wherein the polypeptide is functionally equivalent to the polypeptide consisting of the amino acid sequence of SEQ ID NO: 2; and (c) an amino acid sequence that is at least 60% identical to the amino acid sequence according to (a). The polypeptide (i.e., transcription factor) of the invention herein is capable of binding a nucleic acid sequence of a promoter that is operably linked to at least one gene involved in terpene biosynthesis in the plant. For example, the gene is selected from the group comprising a Terpene Synthase 5 (TPS5) and a Terpene Synthase 11 (TPS11). For example, the promoter comprises a trichome-specific promoter.

An alternative embodiment of the invention provides a method for increasing the production of at least one terpene in a plant, involving up-regulating a transcription factor that positively regulates at least one gene involved in terpene biosynthesis in the plant, such gene preferably being selected from the group comprising TPS5 and TPS11. For example, up-regulating the transcription factor involves modifying the plant to have an increased copy number of a nucleic acid sequence of SEQ ID NO:1, or a sequence with at least 60% identity to the nucleic acid sequence of SEQ ID NO: 1, compared to a non-modified plant of the same genetic background, thereby increasing the level of the at least one terpene in the modified plant.

In a preferred embodiment, a method is provided for increasing the level of at least one terpene in a plant involving: (a) contacting a plant cell or plant protoplast with a composition that includes a vector having a nucleic acid sequence of SEQ ID NO:1 or a fragment thereof with at least 60% identity to the sequence of SEQ ID NO:1; (b) selecting the plant cell or plant protoplast transformed with the vector wherein the plant cell or plant protoplast overexpresses the nucleic acid sequence or the fragment thereof so that overexpression results in an increased level of the at least one terpene in the cell compared to a non-transformed plant cell or plant protoplast; and (c) regenerating the plant from the transformed cell or protoplast wherein the plant has an increased level of the at least one terpene compared to a non-transformed plant of the same genetic background. Within the scope of the invention is also a method for increasing production of at least one terpene in a population of plants by selectively breeding the transformed plant to produce the population of transformed plants having the increased level of the at least one terpene compared to a non-transformed plants of the same genetic background.

In yet another embodiment, a method is provided for reducing production of at least one terpene in a plant that involves down-regulating a transcription factor that positively regulates at least one gene involved in terpene biosynthesis in the plant, wherein the gene preferably is selected from the group comprising TPS5 and TPS11. For example, down-regulating the transcription factor may involve modifying the plant to have a mutation in a nucleic acid sequence of SEQ ID NO: 1 or a sequence with at least 60% identity to the nucleic acid sequence of SEQ ID NO: 1, or a nucleic acid sequence of SEQ ID NO: 3 or a sequence with at least 60% identity to the nucleic acid sequence of SEQ ID NO: 3, wherein the mutation results in a decrease of the level of the transcription factor or a loss of function of the transcription factor, compared to a non-modified plant of the same genetic background, thereby reducing the level of the at least one terpene in the modified plant. For example, the mutation may include a substitution, a deletion, an insertion or an addition of at least one nucleotide. In a related embodiment of the method, down-regulating the transcription factor may involve modifying the plant to have an increased level of RNA having a nucleic acid sequence at least in portion complementary to a nucleic acid sequence of SEQ ID NO: 1, or a sequence with at least 60% identity to the nucleic acid sequence of SEQ ID NO: 1, or a nucleic acid sequence of SEQ ID NO: 3 or a sequence with at least 60% identity to the nucleic acid sequence of SEQ ID NO: 3, compared to a non-modified plant of the same genetic background, thereby decreasing the level of the at least one terpene in the modified plant.

In a particularly preferred embodiment, a method is provided for reducing terpene levels in a population of plants, comprising steps of: (a) providing at least one plant within a population of plants comprising a mutation in a gene comprising a nucleic acid sequence of SEQ ID NO: 1 or a nucleic acid sequence with at least 60% identity to the nucleic acid sequence of SEQ ID NO: 1, or a nucleic acid sequence of SEQ ID NO: 3 or a nucleic acid sequence with at least 60% identity to the nucleic acid sequence of SEQ ID NO: 3; and (b) selectively breeding the at least one mutant plant of (a) to produce the population of plants having the reduced terpene levels.

In particular, the terpene of the method includes at least one of a monoterpene and a sesquiterpene that repel insects. For example, the monoterpene includes at least one compound selected from the group of: linalool, β-myrcene, para-cymene, γ-terpinene, α-terpinene, and α-phellandrene. For example, the sesquiterpene comprises at least one compound selected from the group of: nerolidol, germacrene, R-curcumene, S-curcumene and 7-epizingiberene.

Alternatively, the terpene of the methods herein includes at least a monoterpene and a sesquiterpene that attract insects. For example, the monoterpene includes at least one compound selected from the group of: β-phellandrene, limonene and 2-carene. For example, the sesquiterpene comprises at least β-caryophyllene.

Generally, the invention herein is concerned with attracting or repelling insects including sap-sucking insects and blood-sucking insects. For example, the sap-sucking insects include psyllids, whiteflies, aphids, mealybugs, plant hoppers and scale insects. For example, the blood sucking insects comprise mosquito, ticks and midges. Insects including thrips, mites and leaf hoppers are also within the scope of the invention.

Generally, the plant of the methods of the present invention is at least one crop plant selected from the group of: tomato, pepper, eggplant, lettuce, oilseed rape, broccoli, cauliflower, cabbage crops, cucumber, melon, pumpkin, squash, peanut, soybeans, corn, cotton, beans, cassava, potatoes, sweet potatoes and okra. The plant also includes at least one plant selected from a Solanaceae family. The methods herein may also be directed at least one ornamental plant selected from the group of: hibiscus, poinsettia, lily, iris, rose and petunia.

An embodiment of the invention also provides a plant obtainable or obtained by the methods described herein. Additionally, the invention pertains to a plant comprising a chimeric gene as provided herein. Such plant may be a genetically engineered plant comprising a nucleic acid sequence of SEQ ID NO:1 and variants and fragments thereof. For example, the plant may belong to the Solanaceae family.

A tissue culture initiated from the plants described herein, e.g., a transformed or modified plant, also is within the scope of the invention. Such tissue culture has enhanced production or secretion of at least one terpene, terpene isomer, or terpene analog.

A related embodiment provides a method for producing a terpene, terpene isomer, or terpene analog involving isolating the terpene, terpene isomer or terpene analog from the tissue culture resulting from the transformed plant.

A final embodiment of the invention provides a method for a marker-assisted introgression of a terpene into a plant including the steps of: (a) identifying a difference in a gene encoding an amino acid sequence of SEQ ID NO:2 between a plant from the Solanaceae family and a sexually compatible plant wherein the gene with the difference comprises a molecular marker associated with presence of the terpene in the plant; (b) making a cross between the plant having the molecular marker and the sexually compatible plant; (c) screening a progeny resulting from the cross for the presence of the molecular marker; and (d) identifying the plant within the progeny having the molecular marker and thereby identifying the plant producing the terpene.

BRIEF DESCRIPTION OF THE DRAWINGS

FIG. 3 panel A shows tissue-specific expression of the gene in tomato Money maker leaves, whole stem including trichomes, bald stem and isolated trichomes. The highest level of expression was observed in the isolated trichomes.

FIG. 3 panel B shows trichome expression of the gene in control and jasmonic acid-sprayed plants (JA), (values corrected for actin).

FIGS. 5A, 5B, 5C, 5D, 5E, and 5F show a genomic nucleic acid sequence of SEQ ID NO: 3 encoding the transcription factor TF 19(6). The underlined capital letters herein denote exons and the underlined small letters indicate introns. The capital letters in bold show start and stop codons. The capital letters which are not underlined indicate the putative TF19(6) 4 kb promoter region upstream of the start codon and 2 kb '3 UTR region downstream of the stop codon. The position of the sequences encoding the putative zinc finger motifs are indicated in a light shade of gray.

DETAILED DESCRIPTION OF THE INVENTION

Figure 1:
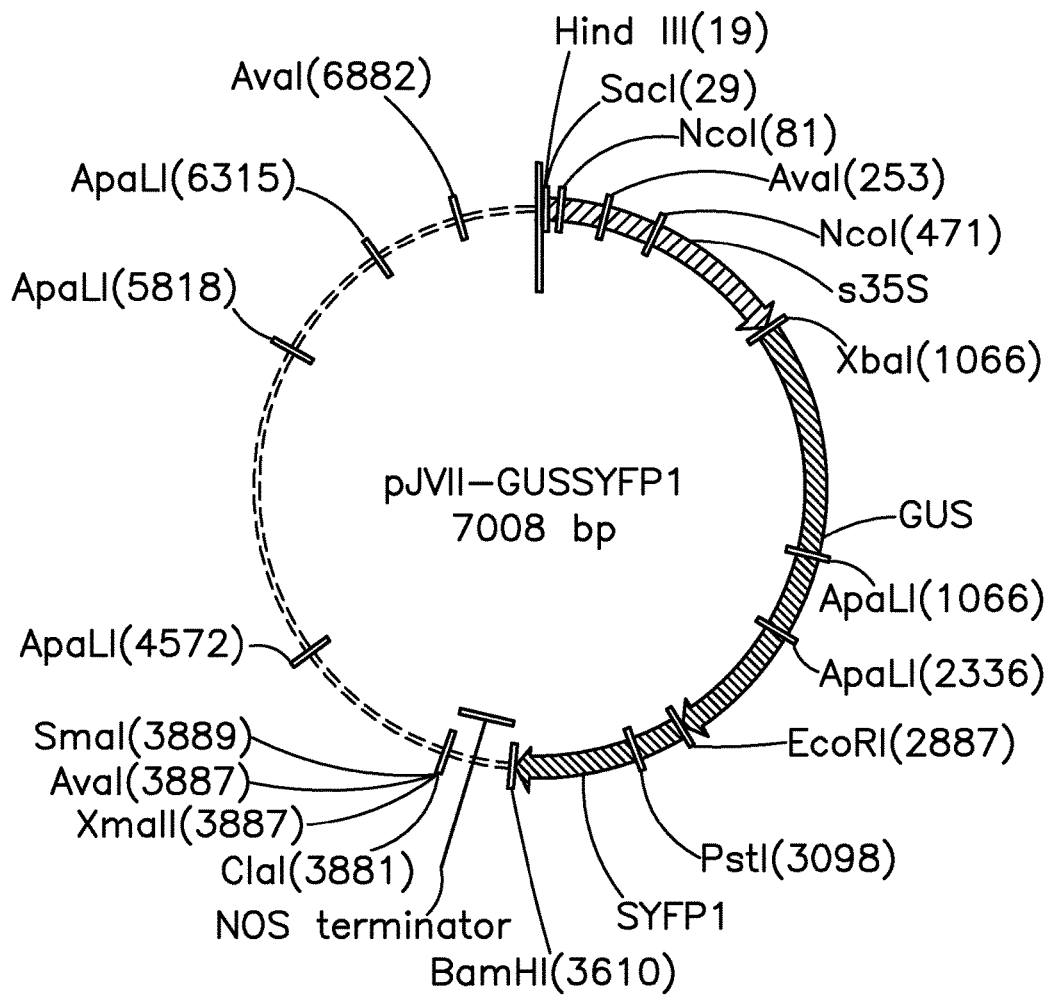
FIG. 1 is a schematic drawing of a PJVII-GUS-sYFP1, a pMON999 vector with a modified multiple cloning site. The *S. lycopersicum* Terpene Synthase 5 (SlTPS5), also referred to as Monoterpene Synthase 1 (SlMTS1), promoter was cloned between SacI and XbaI sites and β-glucuronidase (GUS) fused to a yellow fluorescent protein (sYFP1) was cloned between XbaI and BamHI sites.

The present invention relates to a transcription factor, referred to herein as TF19(6), that regulates terpene biosynthesis in plants. The TF19(6) cDNA comprises a nucleic acid sequence of 1056 bp (SEQ ID NO:1) with a single open reading frame encoding a polypeptide of 351 amino acids (SEQ ID NO:2).

Accordingly, the skilled artisan would understand that by expressing the sequences of the present invention in a plant, one may change the expression of one or more genes involved in terpene biosynthesis. By affecting the expression of the genes, one may alter a plant phenotype to include plants with an improved resistance to insects or other pests and pathogens, or plants attracting beneficial organisms, e.g., predators or parasitoids of pest insects or plant pollinators, or other organisms.

The sequences of the present invention may originate from any species, especially from plant species, or from any other sources including recombinant or synthetic.

The transcription factors of the invention may also include a DNA regulatory sequence that regulates expression of one or more genes in a plant when a transcription factor having one or more domain binding sites binds to the regulatory sequence of one or more genes in the pathway.

The present invention relates also to methods for modifying a plant phenotype by employing one or more polynucleotides or polypeptides of the invention for altering the expression of one or more genes of the terpene biosynthesis pathway. Alternatively, the polynucleotides and peptides of the invention have a variety of additional uses including, without limitation, use as substrates for further reactions such as inducing mutations, performing PCR reactions, use as substrates for cloning including digestion and ligation reactions, identifying exogenous or endogenous modulators of the transcription factors, use in the production of recombinant protein, use as diagnostic probes for the presence of complementary or partially complementary nucleic acids, or the like.

The terpene biosynthesis pathway refers to the pathways leading to the formation of various terpene molecules. The terms "terpenes" and "terpenoids" are used herein interchangeably, and refer to hydrocarbons having a carbon skeleton derived from isoprene units ($C_5H_8$).

Terpenes are subdivided into groups based on their carbon number and may be cyclic or acyclic molecules. The five-, ten-, fifteen-, twenty- and thirty-carbon terpenes are referred to as hemi-, mono-, sesqui-, di-, and triterpenes, respectively.

For example, the term "monoterpenes" refers to a class of terpenes that consists of two isoprene units and have the molecular formula ($C_{10}H_{18}$). Monoterpenes include but are not limited to cyclic monoterpenes, including myrcene, (Z)- and (E)-ocimene, linalool, geraniol, nerol, citronellol, myrcenol, geranial, citral a, neral, citral b, citronellal; monocyclic monoterpenes, including limonene, α- and γ-terpinene, α- and β phellandrene, terpinolene, menthol, carveol; bicyclic monoterpenes including α-pinene, β-pinene, myrtenol, myrtenal, verbanol, verbanon, pinocarveol; and tricyclic monoterpenes, including tricyclene.

As used herein, the term "sesquiterpenes" refers to a class of terpenes that consists of three isoprene units and has the molecular formula $C_{15}H_{24}$. Sesquiterpenes include but are not limited to cyclic sesquiterpenes, including farnesene; monocyclic, including zingiberene and humulene; bicyclic, including caryophyllene, vetivazulene, guaizulene; tricyclic, including longifolene, copaene, patchoulol.

As used herein the term "diterpenes" refers to terpenes consisting of four isoprene units and have the molecular formula $C_{20}H_{32}$. Known diterpenes include, for instance, taxol.

As used herein, the term terpenes refers also to terpene analogs, such as alcohols, aldehydes, ketons and esters, and isomers, including stereoisomers and tautomers.

Reference to specific isomers herein such as α- and/or β-isomers does not preclude the skilled artisan to use other isomers and appreciate that the other isomers or mixtures of isomers can substitute for the isomer specifically mentioned, as long as these are functional.

For example, it was observed that transformed potato and *Arabidopsis* plants overexpressing the Nerolidol Synthase 1 gene from strawberry emitted not only linalool but also linalool derivatives including E-8-hydroxy linalool, Z-8-hydroxy-linalool and E-8-hydroxy-6,7-dihydrolinalool (Aharoni et al., 2006 Phytochemistry Review 5:49-58). Metabolic engineering of terpenoids in plants by overexpressing enzymes catalyzing steps in the terpene biosynthesis pathway was shown to be successful to generate substantial levels of terpenoids (Lewinson et al., 2001 Plant Physiol 127:1256-1264; Aharoni et al., 2003 Plant Cell 15:2866-2884; Lucker et al., 2004 Plant J 39: 135-145; Lucker et al., 2004 Plant Physiol 134: 510-519; Aharoni et al., 2006 Phytochemistry Review 5:49-58). However, manipulation of the expression of the individual genes of the pathways sometimes shows limited success due to lack or poor availability of essential precursors. Regulation of the expression of genes involved in metabolic pathways using transcription factors was shown to modulate additional pathways and lead to availability of precursors (Misra et al., 2010 Plant Physiol 152:2258-2268).

Terpenes are synthesized from the common precursor isopentenyl pyrophosphate (IPP) and its isomer dimethylallyl diphosphate (DMAPP) through two distinct biosynthesis pathways: the mevalonate pathway found in the plants cytosol and in eukaryotes and the deoxyxylulose-5-phosphate (DXP) pathway found in the plant plastids and in prokaryotes. In the mevalonate pathway, the biosynthesis of IPP starts from the conversion of three molecules of acetyl-CoA to mevalonate followed by subsequent sequential phosphorylation of mevalonate to diphosphomevalonate followed by decarboxylation to produce IPP. In the DXP pathway, the production of DXP starts from one molecule each of pyruvate and glyceraldehyde-3-phosphate catalyzed by 1-deoxy-D-xylulose-5-phosphate synthase and results in the production of IPP and DMAPP in contrast to the mevalonate pathway where IPP is the sole product. Generally, sesquiterpenes are synthesized from the relevant precursors through the mevalonate pathway in the cytosol, and monoterpenes and diterpens are produced through the DXP pathway in plastids. Exchange of precursors between plastids and cytosol was also observed.

In both pathways, the IPP is further isomerized to DMAPP by the IPP isomerase with subsequent formation of the higher molecular weight acyclic polyprenyl pyrophosphate precursors by prenyl transferases to form the acyclic pyrophosphate terpene precursors. For example, these reactions produce ten-, fifteen-, and twenty-carbon precursors geranyl-pyrophosphate (GPP), farnesyl-pyrophosphate (FPP), geranylgeranyl-pyrophosphate (GGPP), respectively. Prenyltransferases are divided into two main classes based on stereochemistry of the double bond formed at each elongation cycle. Prenyltransferases leading to the formation of double bonds in cis-configuration are called cis- or Z-prenyltransferases and prenyltransferases leading to the formation of double bonds in trans-configuration are called trans-, or E-prenyltransferases.

Terpene synthases (TPSs) are the enzymes catalyzing the cyclisation of the acyclic precursors in the multi-step reactions producing the carbon skeleton of terpene, monoterpene or sesquiterpene compounds. For example, the initial step of the catalyzed cyclisation may be the ionization of the diphosphate group to form an allylic cation. The substrate then undergoes isomerizations and rearrangements which can be controlled by the active site of an enzyme. The product, for example, may be an acyclic, mono-, di or tricyclic terpene.

It is known in the art that GPP and neryl diphospate (NPP), the cis-isomer of GPP, are the substrates for monoterpene biosynthesis, and that FPP and GGPP are the respective substrates for sesquiterpene synthases and diterpene synthases (Chen et al., 2011 Plant J 66:212-229; Schilmiller et al., 2009 Proc Natl Acad Sci 106:10865-10870; Tholl 2006 Curr Opin Plant Biol 9:297-304; Wang and Ohnuma, 2000 Biochim Biophys Acta 1529:33-48).

Some TPSs produce a single product, but many produce multiple products from the same precursor, or can produce multiple compounds depending on the precursor supplied (Van Schie et al., 2007 Plant Mol Biol 64:251-263).

Induced terpene biosynthesis was observed to correlate with induced expression of terpene synthases (Navia-Gine et al., 2009 Plant Phys Biochem 47: 416-425; Herde et al., 2008 Plant Cell 20: 1152-1168).

Plants emit volatiles consisting of a mixture of mono- and sesquiterpenes to repel pest insects or to attract beneficial insects, e.g., predators or parasitoids of pest insects or plant pollinators. Two terpene synthases TPS5 (formerly Monoterpene Synthase 1, MTS1) and TPS4 (formerly Monoterpene Synthase 2, MTS2) were identified in tomato (Van Schie et al., 2007 Plant Mol Biol 64:251-263; Falahara et al., manuscript in preparation; Bleeker et al., manuscript in preparation). The study shows that TPS5 is expressed in trichomes and that TPS5 protein catalyzes formation of linalool from GPP in vitro. TPS5 expression in tomato trichomes was observed to be low under normal condition and elevated after induction with jasmonic acid (Van Schie et al., 2007 Plant Mol Biol 64:251-263; Kharel and Koyama, 2003 Nat Prod Rep 20:11-118). Van Schie's study also found that TPS4 is expressed in stems, roots and in trichomes and that this gene encodes an enzyme leading to the formation of β-myrcene, β-phellandrene and sabinene from GPP (Van Schie et al., 2007 Plant Mol Biol 64:251-263).

Although monoterpenes appear to dominate terpenes identified in S. lycopersicum, majority of TPS genes mined from tomato genome are sesquiterpene synthases (Falahara et al., manuscript in preparation). Sequencing of cDNAs derived from trichomes of S. lycopersicum and S. habrochaites resulted in identification of multiple TPS sequences having similarities to known sesquiterpene synthases (Bleeker et al., manuscript in preparation). For instance, in S. lycopersicum database, transcripts for TPS9 (formerly germacrene C synthase; van Der Hoeven et al., 2000 Plant Cell 12: 2283-2294), TPS12 (formerly β-caryophyllene/α-humulene synthase; van Der Hoeven et al., 2000 Plant Cell 12: 2283-2294), TPS15, TPS16, TPS17 and TPS31 (formerly LeVS2 because of similarity to vetispiradiene synthase from potato) were identified. In S. habrochaites, cDNA sequences were identified to have similarities to the TPS9, TPS12, TPS14, TPS15 and TPS17.

The compounds which can be regulated by the transcription factor of the present invention include, without limitation, terpene compounds that attract insects such as β-phellandrene, limonene and 2-carene, referred to herein as "attractants". The compounds regulated by the transcription factor of the present invention also include, but are not limited, to terpenes that repel insects such as R-curcumene, S-curcumene, β-myrcene, para-cymene, γ-terpinene, zingiberene, 7-epizingiberene, α-terpinene and α-phellandrene, referred to as "repellents". These compounds are described in the patent application WO 2010/099985 which is incorporated herein by reference.

Additionally, sesquiterpenes present in trichomes of S. lycopersicum cv. Moneymaker and S. hacbrochaites PI127826 can also be regulated by the transcription factor herein (See Table below; Bleeker et al., manuscript in preparation).

TABLE

Sesquiterpenes present in trichomes of S. lycopersicum cv. Moneymaker and S. habrochaites PI127826.

| sesquiterpene | S. lycopersicum | S. habrochaites |
|---|---|---|
| Azulene | x | |
| α-copaene | x | |
| β-elemene | | x |
| caryophyllene | x | x |
| γ-elemene | x | x |
| Alpha humulene | x | x |
| β-farnesene | | x |
| β-acoradiene | | x |
| Curcumene | | x |
| germacrene D | x | x |
| Zingiberene | | x |
| Cuparene | x | |
| β-bisabolene | | x |
| β-sesquiphellandrene | | x |
| Valencene | | x |
| germacrene C | x | |
| selina-3.7(11)-diene | | x |
| germacrene B | | x |

Trichome-specific promoters were identified in tomato that regulate expression of the TPS5 and TPS11 genes. (The TPS5 promoter was referred to as the MTS1 promoter and the TPS11 promoter was referred to as the STS1 promoter in the international patent application WO 09/082208 incorporated herein by reference).

As used herein, the term "promoter" refers to a nucleic acid sequence that is capable of initiating transcription of a nucleic acid sequence to which it is operably linked. The promoter controls transcription of one or more genes, located upstream of the transcription site of the gene. Structurally the promoter is characterized by the presence of a binding site for DNA-dependent RNA polymerase, transcription initiation sites and any other DNA domains (cis regulatory elements), including, but not limited to transcription factor binding sites, repressor and activator protein binding sites, and any other sequences of nucleotides known to one of skill in the art to act directly or indirectly to regulate the rate of transcription from the promoter. Examples of eukaryotic cis regulatory elements include the TATA box located approximately 25 base pairs upstream of the transcription site, the CAAT box located 75-80 base pairs upstream of the initial transcription site, enhancer or silencer elements. The promoters of the invention herein include constitutive promoters that are active in all tissues and organs of the organism but preferably tissue-specific promoters that are active mainly in specific tissues such as trichomes. Especially included are the promoters of Terpene Synthase 5, i.e., linalool synthase, or Monoterepene Synthase 1, and Terpene Synthase 11 found in plants belonging to the genus *Solanum* or other plant species.

Polynucleotides of the Invention

The present invention provides an isolated, recombinant, or synthetic polynucleotide encoding the polypeptide or variant polypeptides of the transcription factor provided herein.

An embodiment of the invention provides an isolated, recombinant or synthetic nucleic acid sequence of SEQ ID NO:1, or a variant thereof which is at least 60%, 65%, 70%, 75%, 80%, 85%, 90%, 92%, 95%, 96%, 97%, 98% or 99% identical to a nucleic acid sequence of SEQ ID NO:1 and which encodes a transcription factor having an amino acid sequence as shown in SEQ ID NO:2, or a fragment or variant thereof that is capable of regulating terpene biosynthesis.

In a further aspect of this embodiment, the nucleic acid sequence encodes a peptide portion of TF19(6) polypeptide having DNA binding activity. Such DNA binding domains binds to a specific target DNA sequence, and have an amino acid sequence that is different from those of known zinc finger domain DNA binding proteins.

In another embodiment, a full length genomic nucleic acid sequence of SEQ ID:NO: 3 is provided that contains coding and non-coding nucleic acid sequences.

The terms "nucleic acid sequence," "nucleotide sequence", "nucleic acid," and "polynucleotides" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. Due to the degeneracy of the genetic code various nucleic acid sequences may encode the same amino acid sequence.

Any nucleic acid sequence encoding TF19(6) or variants thereof is referred herein as TF19(6) encoding sequence.

"Isolated" refers to a nucleic acid sequence that is removed from its natural environment and which is substantially free from other nucleic acid sequences, and the nucleic acid sequence does not contain portions of unrelated sequences such as functional genes or polypeptide coding regions. An isolated molecule may be obtained by any methods or combination of methods including molecular biology, biochemical and synthetic techniques.

This limitation does not pertain to nucleic acid sequences encoding genes or coding regions artificially added to the nucleic acid sequence after isolation.

"Recombinant nucleic acid sequence" refers to a combination of nucleic acid sequences that are joined together using recombinant DNA technology.

"Recombinant DNA technology" refers to molecular biology procedures to join together nucleic acid sequences as described for instance in Laboratory manuals edited by Weigel and Glazebrook, 2002 Cold Spring Harbor Lab Press; and Sambrook et al., 1989 Cold Spring Harbor, N.Y.: Cold Spring Harbor Laboratory Press.

A fragment of a polynucleotide of SEQ ID NO:1 refers to a nucleic acid sequence comprising contiguous nucleotides of the polynucleotide of the invention herein that is preferably at least 15 bp, at least 30 bp, at least 40 bp, at least 50 bp and/or at least 60 bp in length.

Preferably the fragment of a polynucleotide comprises at least 25, at least 50, at least, 75, at least 100, at least 150, at least 200, at least 300, at least 400, at least 500, at least 600, at least 700, at least 800, at least 900, at least 1000, at least 1100 contiguous nucleotides of the polynucleotide of the invention. Without being limited, the fragment of the polynucleotides herein may be used as a PCR primer, and/or as a probe, or for anti-sense gene silencing.

The "primer" refers to a short nucleic acid sequence that is hybridized to a template nucleic acid sequence and is used for polymerization of a nucleic acid sequence complimentary to the template.

In a related embodiment of the invention, PCR primers and/or probes for detecting nucleic acid sequences encoding TF19(6) are provided. The skilled artisan would be aware of methods to synthesize degenerate or specific PCR primer pairs to amplify a nucleic acid sequence encoding TF19(6) or fragments thereof, based on SEQ ID NO:1 (see Dieffenbach and Dveksler, 1995 PCR Primer: A Laboratory Manual, Cold Spring Harbor Laboratory Press; McPherson et al., 2000 PCR Basics: From Background to Bench, $1^{st}$ ed., Springer Verlag, Germany). A detection kit for nucleic acid sequences encoding TF19(6) may include primers and/or probes specific for nucleic acid sequences encoding TF19 (6), and an associated protocol to use the primers and/or probes to detect nucleic acid sequences encoding TF19(6) in a sample. Such detection kits may be used to determine whether a plant has been modified, i.e., transformed with a sequence encoding TF19(6).

It is clear to the skilled artisan that mutations, deletions, insertions, and/or substitutions of one or more nucleotides can be introduced into the DNA sequence of SEQ ID NO:1 or shorter fragments thereof. Generally, a mutation is a change in the DNA sequence of a gene that can alter the amino acid sequence of the protein encoded by the gene.

To test a function of a variant DNA sequences according to the invention, the sequence of interest is operably linked to a selectable or screenable marker gene and expression of the reporter gene is tested in transient expression assays with protoplasts or in stably transformed plants. It is known to the skilled artisan that DNA sequences capable of driving expression are built as modules. Accordingly, expression levels from shorter DNA fragments may be different than the one from the longest fragment and may be different from each other. Embraced by the present invention are also functional equivalents of the nucleic acid sequence coding the transcription factor of the present invention, i.e., nucleotide sequences that hybridize under stringent conditions to the nucleic acid sequence of SEQ ID NO:1.

A stringent hybridization is performed at a temperature 65° C. and most preferably at 55° C. in double strength (2×) citrate buffered saline (SSC) containing 0.1% SDS followed by rinsing of the support at the same temperature but with a buffer having reduced SSC concentration.

Such reduced concentration buffers are typically one tenth strength SSC (0.1×SSC) containing 0.1% SDS, preferably 0.2×SSC containing 0.1% SSC and most preferably half strength SSC (0.5×SSC) containing 0.1% SDS. Functional equivalents of the transcription factor from other organisms can be found by hybridizing a nucleic acid sequence with SEQ ID NO:1 with genomic DNA isolated from other organisms. The skilled artisan knows methods to identify homologous sequences in other organisms. Such newly identified DNA molecules then can be sequenced and the sequence can be compared with the nucleic acid sequence of SEQ ID NO:1 and tested for functional equivalence. Within the scope of the present invention are DNA molecules having at least 60%, 70%, or 75%, preferably 80%, more preferably 90% and most preferably 95%, 96%, 97%, 98%, 99% or more sequence identity to the nucleotide sequence of SEQ ID NO:1.

The percentage of sequence identity between two sequences is determined using computer programs that are based on standard alignment algorithms. Sequences are substantially identical when they share at least a certain minimal percentage of sequence identity as identified by standard computer programs. Preferably, the sequence identity refers to the sequence identity over the entire length of the sequence.

A related embodiment of the invention provides a nucleic acid sequence which is complementary or reverse complementary to the nucleic acid sequence according to SEQ ID NO:1, such as inhibitory RNAs, or a nucleic acid sequence which hybridizes under stringent conditions to at least part of the sequence according to SEQ ID NO:1 or the reverse complementary sequence to SEQ ID NO:1 (e.g., the non-coding DNA strand).

The polynucleotides of the invention may be overexpressed in plant cells and the changes in the expression levels of a number of genes and/or proteins of the plant cells may be observed. Therefore, polynucleotides and polypeptides of the invention may be employed to change the expression of the genes and/or protein in plants, especially the genes and/or proteins of the terpene biosynthesis. Alternatively, polynucleotides or polypeptides may be employed in knockout plants that lead to changes in the expression levels of one or more genes to improve characteristics or traits of the plants especially traits associated with insect resistance.

The term "gene" means a DNA sequence comprising a region, which is transcribed into a RNA molecule, e.g., a mRNA in a cell, operably linked to suitable regulatory regions, e.g., a promoter. A gene may thus comprise several operably linked sequences, such as a promoter, a 5' leader sequence comprising e.g. sequences involved in translation initiation, a coding region of cDNA or genomic DNA, introns, and a 3'non-translated sequence comprising, e.g., transcription termination sites.

A "chimeric gene" or "recombinant gene" refers to any gene, which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription).

A "3' UTR" or "3' non-translated sequence" (also referred to as 3' untranslated region, or 3'end) refers to the nucleic acid sequence found downstream of the coding sequence of a gene, which comprises for example a transcription termination site and (in most, but not all eukaryotic mRNAs) a polyadenylation signal (such as AAUAAA or variants thereof). After termination of transcription, the mRNA transcript may be cleaved downstream of the polyadenylation signal and a poly(A) tail may be added, which is involved in the transport of the mRNA to the site of translation, e.g., cytoplasm.

As used herein, a molecular marker refers to any morphological, biochemical or nucleic acid based phenotypic difference that reveals a DNA polymorphism. Examples of molecular markers include, but are not limited to, AFLPs (amplification fragment length polymorphisms), RFLPs (restriction fragment length polymorphisms), SNPs (single nucleotide polymorphisms), SSRs (single sequence repeats), and alike. For instance, the skilled artisan would understand how to detect a genomic polymorphism between *Solanum lycopersicum* and sexually compatible species comprising identifying a difference in a gene encoding an amino acid sequence of SEQ ID NO:2 and fragments thereof between the species and thus identifying a molecular marker. For example, a molecular marker can be identified in at least one of a nucleic acid sequence of SEQ ID NO: 1 and a nucleic acid sequence of SEQ ID NO: 3. The molecular marker so identified can be used in marker-assisted selection of plants having the desired composition of terpenes that repel or, alternatively, attract insects, or other organisms.

Polypeptides of the Invention

An embodiment of the present invention provides a transcription factor, transcription factor homologous polypeptides, and variants thereof.

The phrase "transcription factor" refers to a protein that regulates expression of one or more genes involved in terpene biosynthesis in an organism. The transcription factor possesses one or more domains for binding DNA regulatory sequences and at least one conserved domains characteristic of a particular family of transcription factors. Transcription factors encompass transcription factors-activators stimulating expression of one or more genes involved in terpene biosynthesis and transcription factors-suppressors inhibiting transcription of the genes by binding to their regulatory sequences.

"Zinc finger protein transcription factor" refers to an activator or a repressor composed of a zinc finger protein domain and any of a variety of transcription factor effectors domains which effect or modulate expression of nucleic acid sequences in the vicinity of zinc finger protein binding site. Zinc finger domains generally are about 25 to 30 amino acid residues in length, and contain high number of cystein residues in a C-Xn-C-Xn-C-Xn-C-Xn-C-type motif where X denotes a variable amino acid and n indicates the number of X residues. X residues are generally polar and basic, and implicate the region as involving in binding nucleic acids. Zinc ions are essential components of zinc finger domain structure designed to interact and bind nucleotides of a nucleic acid molecule.

A protein is an amino acid sequence of any length linked by covalent peptide bonds, and includes oligopeptide, peptide, polypeptide and full length protein whether naturally occurring or synthetic. A polypeptide means an amino acid sequence of consecutively polymerized amino acid residues, for instance, at least 15 residues, at least 30 residues, at least 50 residues.

The term "isolated" polypeptide refers to an amino acid sequence that is removed from its natural environment by any method or combination of methods known in the art and includes recombinant, biochemical and synthetic methods.

An embodiment of the invention provides an isolated or recombinant polypeptide which has an amino acid sequence set forth in SEQ ID NO:2 or fragments, or variants or derivatives thereof.

The term "fragment" of the polypeptide of SEQ ID NO: 2 refers to a subsequence of the polypeptide of the invention that retains its biological function and capacity to alter transcript levels of the genes of the terpene biosynthesis pathways, and is preferably capable of binding a nucleic acid sequence of a promoter that is operably linked to at least one gene selected from the group comprising a Terpene Synthase 5 (TPS5) and a Terpene Synthase 11 (TPS11). The term may refer to a recombinant polypeptide and/or an aggregate polypeptide such as a dimer or multimer.

As used herein, the terms "variant" or "derivative" of the polypeptide set forth in SEQ ID NO:2 refers to polypeptides with substantial similarity of amino acid sequences to the polypeptide herein. The amino acid sequences of the polypeptide of the invention and variants thereof may differ by one or more deletions, additions, and/or substitutions of amino acids while retaining functional equivalence to the polypeptide. In one embodiment, variants of TF19(6) include, for example, proteins having at least 60%, 65%, 70%, 75%, 80%, 85%, 90%, 92%, 95%, 96%, 97%, 98%, 99% or more amino acid sequence identity over the entire length to SEQ ID NO:2. Amino acid sequence identity may be determined by pairwise alignment using the Needleman and Wunsch algorithm and GAP default parameters.

Variants also include proteins capable of binding a promoter sequence operably linked to another nucleic acid sequence preferably of a gene that regulates terpene biosynthesis, such as TPS5 and/or TPS11, which have been derived, by way of one or more amino acid substitutions, deletions or insertions, from the polypeptide having the amino acid sequence of SEQ ID NO:2. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions. For instance, amino acids of the polypeptide of the invention may be modified based on similarity in hydrophobicity, hydrophilicity, solubility, polarity of amino acid residues, as long as the variant polypeptide remains functionally equivalent to the polypeptide of the invention. Alternatively, a variant may differ from the polypeptide of the invention by attachment of modifying groups which are covalently or non-covalently linked to the polypeptide backbone. The variant also includes a polypeptide which differs from the polypeptide of the present invention by introduced N-linked or O-linked glycosylation sites, and/or an addition of cysteine residues. The skilled artisan would understand how to modify an amino acid sequence and preserve biological activity using computer programs such as DNASTAR (Madison, Wis., USA).

A variant or derivative of zinc finger polypeptide of the invention retains a capacity to alter transcript levels of the genes of the terpene biosynthesis pathways, including or in particular the transcript levels of the genes encoding a Terpene Synthase 5 (TPS5) and/or Terpene Synthase 11 (TPS11).

The polypeptide of the invention is capable of binding a promoter sequence operably linked to another nucleic acid sequence preferably of a gene that regulates terpene biosynthesis, such as TPS5 and/or TPS11.

A nucleic acid sequence encoding the polypeptide of the invention is "operably linked" to another nucleic acid sequence, typically a coding gene, when the gene so linked is transcribed. Operably linked DNA sequences form contiguous reading frames to produce a "fusion protein," i.e., a protein composed of various protein "domains" or "motifs." The nucleotide sequence associated with the promoter sequence may be of homologous or heterologous origin with respect to the plant to be transformed. The sequence may be also entirely or partially synthetic. Regardless of the origin, the nucleic acid sequence associated with the promoter sequence will be expressed or silenced in accordance with promoter properties to which it is linked after binding to the polypeptide of the invention.

In a preferred embodiment of the invention, the associated nucleic acid may code for a protein that is desired to be expressed or suppressed throughout the plant at all times or, alternatively, in specific cells and tissues. Such nucleotide sequences preferably encode proteins conferring desirable phenotypic traits to the plant modified or transformed therewith.

More preferably, the associated nucleotide sequence leads to the production of terpenes in the plant. Preferably, the nucleotide sequence encodes TPS5 or TPS11 and terpenes that confer insect resistance, disease resistance, resistances to other pests and/or attraction of beneficial organisms, e.g., predators or parasitoids of pest insects or plant pollinators.

Homologous Polynucleotides and Polypeptides

Homologs, paralogs, orthologs and any other variants of the sequences herein are expected to function in a similar manner by making plants that repel or resist insects, or alternatively, attract beneficial organisms, e.g., predators or parasitoids of pest insects or plant pollinators. Homologous sequences are sequences that share substantial sequence identity or similarity to the nucleic acid sequence of SEQ ID NO:1. Homologous sequences may be derived from any plants including monocots or dicots, and especially crops including but not limited to tomato, pepper, eggplant, lettuce, sunflower, oilseed rape, broccoli, cauliflower and cabbage crops, cucumber, melon, watermelon, pumpkin, squash, peanut, soybeans, cotton, beans, avocado, onion, endive, leek, roots such as arrowroot, carrot, beet, turnip, radish, yam, cassava, potatoes, sweet potatoes and okra. Homologous sequences may also be derived from crop species including maize, barley, pearl millet, wheat, rye, sorghum, rice, tobacco and forage grasses. Homologous sequences may be derived from tree species and fleshy fruit species such as lemons, tangerines, oranges, grapes, peaches, plums, currant, cherries, melons, strawberry, and mango, or from ornamental plant species such as hibiscus, poinsettia, lily, iris, rose and petunia, and the like. Additionally, homologous sequences may be derived from plant species that are wild relatives of crop plant species.

For example, homologous sequences may be derived from nightshade *Atropa belladonna* which is a wild relative of a cultivated tomato *Solanum lycopersicum*, or teosinte species related to maize.

Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise BLAST® (Basic Local Alignment Search Tool) analysis (Feng and Dollitle, 1987 J Mol Evol: 25:351-360) or during phylogenetic analysis of gene families using programs such as CLUSTAL (Thompson et al., 1994 Nucl. Acid Res 22:4573-4680; Higgins et al., 1996 Methods Enzymol 266: 383-402). In paralogs, consensus sequences can be identified characteristic to sequences within related genes and having similar functions of the genes.

Genes encoding regulatory elements and transcription factors are conserved in eukaryotes. For instance, plant species that have common ancestors are known to contain many transcription factors that have similar sequences and functions. These sequences are referred to as orthologs. The skilled artisan can identify orthologous sequences and predict the functions of the orthologs, for example, by constructing a polygenic tree for a gene family of one species using CLUSTAL or BLAST® (Basic Local Alignment Search Tool) programs.

A method for identifying or confirming similar functions among homologous sequences is by comparing of the transcript profiles in plants overexpressing or lacking (in knockouts/knockdowns) related polypeptides. The skilled artisan will understand that genes having a similar transcript profiles, with greater than 50% regulated transcripts in common, or with greater than 70% regulated transcripts in common, or greater than 90% regulated transcripts in common will have similar functions.

Homology refers to a sequence similarity, or identity between a polypeptide or a fragment thereof and a references sequence. A homology of polypeptide sequences are determined based on the number of amino acid sequences in the positions shared by the polypeptides. Homologous sequences encompass amino acid sequences of polypeptide of the present invention modified by chemical or enzymatic means known in the art. See Ausubel et al. (eds) 2000 Current Protocols Mol Biol, Willey & Sons, New York.

Polypeptides with "substantial identity" refers to sequences of sufficient similarity to the transcription factor of SEQ ID NO:2 which retains biological function of the transcription factor when overexpressed, ectopically expressed or knocked out in a plant. Polypeptide sequences that are at least 50% identical to the polypeptide of the present invention are considered sufficiently identical.

Regulation of Terpene Biosynthesis

An embodiment of the invention provides a polypeptide, a polynucleotide, a fragment thereof or a chimeric gene or vector that may be used to up- or down regulate expression of genes involved in terpene biosynthesis, preferably selected from at least one of Terpene Synthase 5 (TPS5) and Terpene Synthase 11 (TPS11), and thereby modify downstream products of the pathway.

For example, a polypeptide, a polynucleotide, a fragment thereof or a vector of the invention is used to regulate volatiles emitted by plants to repel pest insects or to attract beneficial insects, e.g., predators or parasitoids of pest insects or plant pollinators, or to regulate the transcription level of the genes involved in the terpene biosynthesis and to alter transcript profiles of such genes. An altered transcript profile of the gene refers to the transcript profile that is substantially different from the transcript profile of the correspondent gene in a reference state. Differences and similarities between expression levels are evaluated by statistical methods known in the art.

An embodiment of the invention provides methods to modify terpene levels in a plant by up- and down regulating expression of TPS5 and TPS11 genes and thereby modifying levels of at least one terpene form a group of: linalool, neralidol, germacrene, α-humulene, β-caryophyllene, β-elemene, β-phellandrene, limonene, 2-carene and zingiberene (7S configuration), β-curcumene, β-myrcene, para-cymene, γ-terpinene, 7-epizingiberene, α-terpinene and α-phellandrene.

A related embodiment of the invention provides a method for increasing a terpene in a plant by up-regulating a transcription factor of the invention that positively regulates terpene biosynthesis. For instance, up-regulating may increase the level of terpenes which are part of chemical defense of the plants and thereby repel insects or pathogenic organisms.

In yet another embodiment, the invention provides a method for reducing a terpene in a plant by down-regulating a transcription factor that positively regulates terpene biosynthesis.

For instance, down-regulation may change the profile of the volatile terpene compounds emitted by the plants thereby making the plants less attractive to insects or other pests Generally, methods for up- and down-regulation of expression of transcription factors in plant or animal systems are well known to the skilled artisans. Up-regulation may result from overexpression of a protein or polypeptide in a whole plant, plant cells or specialized plant tissues, such as trichomes. Alternatively, the promoter may be altered to up-regulate expression of transcription factors of the invention.

Down-regulation occurs at DNA level by interfering with transcription of the genes thereby decreasing expression of the genes. Alternatively, down-regulation occurs at RNA level by interfering with protein translation from RNA molecules, or by interfering with RNA splicing to produce mRNA species. Down-regulation at RNA level is achieved through RNA interference (RNAi) approach using double stranded RNAs (dsRNAs), small hairpin RNAs (shRNAs), micro RNAs (miRNAs) or small interfering RNA (siRNAs). Phenomenon of RNA interference is also known in the art as cosuppression, post transcriptional gene silencing, and quelling. See Hamilton and Baulcombe, 1999 Science 286: 950-952; Hammond and Hannon, 2001 Nature Rev Gen 2: 110-119; Baulcombe, 2007 Science 315:199-200.

An embodiment of the invention provides a method for reducing terpene levels in a population of plants by providing plants mutagenized by either chemical or physical methods, detecting a mutated plant within a population such that the plant has decreased expression of the transcription factor of the invention that positively regulates terpene biosynthesis and selectively breeding the mutated plant to produce the population of mutated plants thereby reducing terpene levels in the plants. An alternative method is provided for increasing terpene levels in a plant population by detecting and selecting a mutated plant within the population that has decreased expression of the transcription factor that negatively regulates terpene biosynthesis.

For example, methods for the detection of a mutation in a target sequence in a member of a mutagenized population is disclosed in WO 2007/037678. The method involves isolating DNA of mutagenized plants, pooling DNA, amplifying the target sequence, i.e., the nucleic acid sequence of TF19(6) with a pair of primers from the DNA pool, determining the nucleic acid sequences of the amplification fragments using high throughput sequencing, identifying mutations by clustering (aligning) the sequences of the fragments, screening the identified mutations for modified functions of the target sequence and identifying members carrying the mutation.

The sequencing may be conducted by methods known in the art, including the dideoxy chain termination method (Sanger sequencing), and high-throughput sequencing methods, such as the methods disclosed in WO 03/004690, WO 03/054142, WO 2004/069849, WO 20041070005, WO 2004/070007, and WO 2005/003375, by Seo et al. (2004) Proc. Natl. Acad. Sci. USA 101:5488-93, and technologies of Helios, Solexa, US Genomics, and the like, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375, which are herein incorporated by reference.

An alternative embodiment of the invention provides a method to alter gene expression in a plant, plant tissue or plant cell. For instance, the polynucleotide of the invention may be overexpressed in a plant, cell or tissue. The term "overexpresssion" refers to an increased expression of a gene in a plant, tissue or a plant cell compared to expression in a non-altered or wild type plant, tissue or cell, at any stage of development or location of the gene. Overexpression occurs when gene encoding transcription factor of the invention is under control of a strong constitutive or a tissue specific promoter.

Alteration of expression of a polynucleotide of the present invention also results in "ectopic expression" which is the different expression pattern in a transgenic or mutant plant and in a control or wild-type plant. Alteration of expression occurs from interactions of polypeptide of the invention with exogenous or endogenous modulators, or as a result of chemical modification of polypeptide. The term also refers to an altered expression pattern of the polynucleotide of the invention which is altered below the detection level or completely suppressed activity.

An alternative embodiment of the invention provides a method for increasing production or level of a terpene in a population of plants including the following steps: contacting a plurality of plant cells with a composition which includes a vector incorporating a nucleic acid molecule set forth in SEQ ID NO:1; detecting and selecting a transgenic plant cell within the plurality of the cells such that the cell has an increased level of a transcription factor that positively regulates terpene biosynthesis compared to a control plant cell thereby increasing the terpene in the cell; regenerating the cell into a plant and selectively breeding the plant to produce the population of plants with the increased terpene.

The vectors for inserting transgenes into the genome of host cells are well known in the art.

As used herein, the term "vector" refers to a nucleic acid molecule engineered using molecular biology methods and recombinant DNA technology for delivery of foreign or exogenous DNA into a host cell. Typically the vector is a DNA molecule that consists of a transgene insert and a nucleic acid backbone. Vectors include plasmids, viruses, cosmids and artificial chromosomes. Binary or co-integrated vectors into which a chimeric gene is inserted may be used for transforming plants.

The chimeric gene generally includes a promoter sequence operably linked to a nucleic acid sequence of a coding gene to be transcribed in the host cells. Alternatively, the promoter sequence may already be present in a vector so that the nucleic acid sequence which is to be transcribed is inserted into the vector downstream of the promoter sequence. Vectors are typically engineered to have an origin of replication, a multicloning site and a selectable marker.

Examples of selectable markers are described below. The skilled artisan would know that different antibiotic or herbicide selectable marker are applicable to different target species.

Selectable markers that are routinely used in plant transformation include the npt II gene conferring resistance to kanamycin, paromymycin, geneticin, and related antibiotics (Veira and Messing, 1982 Gene 19: 259-268; Bevan et al., 1983 Nature 304: 184-187) the bacterial aadA gene encoding aminoglycoside 3'-adenyltransferase conferring resistance to antibiotics streptomycin or spectinomycin (Goldschmidt-Clermont, 1991 Nucl Acid Res 19: 4083-4089), the hph gene conferring resistance to hygromycin (Blochlinger and Diggelmann, 1984 Mol Cell Biol 4: 2929-2931). Other markers that can be used include a mutant EPSP gene conferring resistance to glyphosate (Hinchee et al., 1988 Biotechnology 6: 915-922), a mutant acetolactate synthase (ALS) gene conferring resistance to imidazoline or sulphonylurea herbicides (Lee at all., EMBO Journal 7: 1241-1248), a phospinothricin acetyltransferase gene which confers resistance to herbicide phosphinothricin (White at al., 1990 Nucl Acid Res 18: 1062; Spencer et al., 1990 Theor Appl Genet 79: 625-631). Selection markers resulting in positive selection such as phosphomannose isomerase gene are also used (see WO 93/05163).

An embodiment of the invention provides recombinant expression vectors comprising a nucleic acid sequence of the invention fused to associated nucleic acid sequences such as, for instance, promoter sequences. The vector is used to transform the host cells and the chimeric gene is preferably inserted in the nuclear genome or into the genome of cell organelles, i.e., mitochondria or plastids, such that the expression of the nucleic acid sequence is driven by the activity of the promoter. See *Arabidopsis*, A Laboratory Manual Eds. Weigel and Glazebrook, Cold Spring Harbor Laboratory Press (2002) and Maniatis et al., Molecular Cloning, Cold Spring Harbor Laboratory Press (1982).

Methods for obtaining transgenic plant cells and plants are well known in the art and include but are not limited to *Agrobacterium*-mediated transformation of plant explants, particle bombardment of plant explants, transformation of plant explants using whiskers technology, transformation using viral vectors, electroporation of plant protoplasts, direct uptake of DNA by protoplasts using polyethylene glycol, microinjection of plant explants and/or protoplasts. *Agrobacterium*-mediated transformation is a preferred method to introduce the nucleic acid molecule of the invention into plant explants. *Agrobacterium tumefaciens* harbors a natural vector called Ti plasmid which was engineered to make it suitable for introduction of exogenous nucleic acid molecules into plant genomes. For genetic transformation, plant-derived explants are incubated with suspension of *Agrobacterium* cells followed by cultivation of the explants on the medium containing a selective agent that promotes growth and regeneration of the transformed cells only.

Methods for detecting transformed or modified plant include without limitation, Southern Blot Analysis and PCR based methods. Methods for analyzing terpene content in modified plants using gas chromatography-mass spectrometry (GC-MS) are known in the art and are described in Schilmiller et al., 2009 Proc Natl Acad Sci 106:10865-10870 and Adams, 2007 Identification of Essential Oil Components by Gas Chromatography/Mass Spectrometry, $4^{th}$ ed., Allured Pub Corp., Carol Stream, Ill. The resulting transformed or modified plant may be used in a conventional breeding to produce more transformed or modified plants with altered profile of terpene compounds.

An embodiment of the invention provides antibodies specific for polypeptides of the invention or variants thereof. The skilled artisan would understand that the transcription factor or variants thereof can be expressed and purified in a heterologous expression system, for instance *Escherichia coli*, and used to raise monoclonal or polyclonal antibodies specific for polypeptides of the invention. Antibodies can be also raised against synthetic polypeptides from the amino acid sequences of the transcription factor or variants thereof.

Methods of raising antibodies are known in the art and described in Harlow and Lane, 1988 Antibodies: A Laboratory Manual, Cold Spring Harbor Laboratory, New York. Such antibodies are used to screen expression libraries from the plants and may be used, for example, in a method for identifying plants emitting volatiles that attract beneficial insects or alternatively repel pest insects.

Host Cells, Plants and Tissue Cultures of the Invention

A phrase "host cell" or "transformed cell" refers to a genetically engineered cell that includes at least one nucleic acid molecule, especially a chimeric gene encoding a desired protein or a nucleic acid sequence which upon transcription yields a terpene useful to repel or attract insect pests. The host cell is preferably a plant cell, but may also be a fungal cell, a yeast cell or a bacterial cell. The host cell preferably includes the chimeric gene integrated into the nuclear or organelle genomes, but may also contain the gene extra-chromosomally.

An embodiment of the invention herein also provides a genetically engineered plant cell that includes a nucleic acid sequence set forth in SEQ ID NO:1 and a plant regenerated from the cell. A genetically engineered plant of the invention includes the plant having an increased level of a terpene compared to a non-genetically engineered plant of the same genetic background. As used herein a genetic background refers to the genotypic base of a breeding line or population of organisms.

A related embodiment of the invention also provides for a tissue culture obtained from the transgenic plant such that the culture has enhanced production or secretion of terpene, terpene isomer or terpene analog, and a method for isolating the same from the tissue culture of the invention.

Suitable cells for expression of a polypeptide of the invention include prokaryotic and eukaryotic cells such as plant cells. Plants suitable for expression of a polypeptide of the invention include, but are not limited to crop species, which are natural hosts of insect pests such as tomato, pepper, eggplant, lettuce, sunflower, oilseed rape, broccoli, cauliflower and cabbage crops, cucumber, melon, watermelon, pumpkin, squash, peanut, soybeans, cotton, beans, cassava, potatoes, sweet potato and okra. Crop species also include maize, barley, pearl millet, wheat, rye, sorghum, rice and forage grasses. Additionally, plant hosts include tree species, fleshy fruit species such as grapes, peaches, plums, strawberry and mango, and ornamental species such as hibiscus, poinsettia, lilies, iris, rose and petunia.

Especially preferred are plants belonging to the family Solanaceae, including plants that belongs to genera *Solanum, Capsicum, Nicotiana, Petunia*, and the like. In a preferred embodiment, vegetable species especially of genus *Solanum* are included, for example, tomato (*S. lycopersicum*), eggplant (*S. melongena*), pepino (*S. muricatum*), and the like.

As used herein, the phrase "crop species" refers to plants cultivated for purposes of obtaining food, feed or plant derived products including carbohydrates, oils and medicinal ingredients.

Insects Controlled by Regulation of Terpene Levels in Plants

An embodiment of the invention provides a method for increasing resistance to a pest insect by down regulating or alternatively up regulating the genes of the terpene biosynthesis which would result in altering profiles of volatile terpenes emitted by plants to attract beneficial insects or repel pest insects.

As used herein, the phrases "plant insects" or "plant pests" refer to insect species that infest and damage host crop and ornamental plants. An "infestation" refers to presence of a large number of pest organisms in a field or greenhouse, on the surface of a host plant or on anything that might contact a host plant, or in the soil. Insect pests include sap-sucking insect pests, such as psyllids, whiteflies, aphids, mealybugs, plant hoppers and scale insects and share a common property, namely the utilization of plant sap as their food source. Insect pests also include thrips, cicada, mites and leaf hoppers.

The term "whitefly" or "whiteflies" refers to species of the genus *Bemisia*, especially *B. tabaci*, species of the genus *Trialeurodes*, especially greenhouse whitefly *T. vaporariorum* and banded winged whitefly *T. abutinolea*. All biotypes of *B. tabaci* such as biotype Q and B, are also included as well as any developmental stage, such as eggs, larvae, pupae and adults.

As used herein, the term "aphids" refers to plant insect pests belonging to the family Aphididae, including but not limiting to *Aphis gossypii, A. fabae, A. glycines, A. nerii, A. nasturtii, Myzus persicae, M. cerasi, M. ornatus, Nasonovia* especially *N. ribisnigri, Macrosiphum*, and *Brevicoryne*.

The term "insect pests" also refers herein to insects of the order Diptera including but not limiting to blood sucking or biting insects attacking animals, especially mammals. Blood sucking ticks are also included. Such insects may act as vectors of human and/or mammalian diseases such as malaria.

"Insect vectors" are insects that are capable of carrying and transmitting viruses to plants. In the context of mammalian disease vectors, insect vectors are insects which attack mammals and can potentially transmit diseases to mammals, such as mosquitoes, which are able to transmit the parasite *Plasmodium* to humans or heartworm to canines.

Preferably, the modified plants of the invention develop enhanced resistance to one or more pest insects.

"Insect pest resistance" is an enhanced ability of modified plants of the present invention to withstand attacks of one or more pests compared to wild type or control plants. Methods to assess insect pest resistance in plants are known in the art. For example, disease symptoms may be scored visually at one or more time points after infestation or contact with an insect pest. Alternatively, insect pests may be detected and optionally quantified during infestation of the plants in an assay. A modified plant shows enhanced pest resistance if the number of insect pests detected in the tissue is significantly lower compared to the number of insects detected in control. Preferably, a significant increase in average yield of modified plants of the present invention compared to control (e.g. at least 1%, 2%, 5%, 10% or more) when plants are grown under insect pet pressure provides an indirect measurement of enhanced resistance to pest insects. Statistical analyses are employed to determine existence of significant differences.

The invention now having been fully described it is exemplified in the Examples below and in the claims, which are not to be construed as further limiting. References cited herein are hereby incorporated by reference in their entireties.

Sequences referred to herein:

A nucleotide sequence of SEQ ID NO:1 encoding a transcription factor TF19(6):

```
ATGGCTAATTTCTTTTCATTAGGTGGGAATCAAGAACAACAACATCAAGAAATTAGCAGC

AGCCAAGCATTAGTACCCACAGAGAGTAATAATTGGTTTTTGTACAGAAATGAACATCAT

CATCATCATCATAATCAAGAAATACCCAACACTTACAAAGGTTTTGAGTTATGGCAAAGT

GGTAACACTCCACAACACCAACACCAACACCACCAACAACAACAACAGTTTCGTCATCC
```

```
GATTTATCCTTTGCAAGATCTTTATTCCACTGATGTTGGATTAGGGGTTGGGCCAAGCAG

AAGTGGCTTTGATATATCTGCAGGTGATCATGAGGCGTCGAGGTCGGGATTCGTGATGA

TGAGGAGTGGTGGAGGAGGAATAAGTTGCCAAGATTGTGGGAACCAAGCTAAGAAAGA

TTGTCAACATATGAGGTGTAGGACTTGTTGTAAGAGTAGAGGGTTTCAGTGTCAAACTCA

TGTGAAAAGTACTTGGGTTCCAGCAGCTAAAAGGAGAGAAAGGCAACAACAACTTGCTG

CTTTGCAACAACAACAAGGACATAATAATAATAATAATAATCATAAGAATAAAAGGC

AAAGGGAGGATCCAAGTGCTTCTTCTCTTGTGTCTACTCGTTTGCCTTCAAACACTAATG

GGTTAGAAGTGGGAAAATTTCCATCAAAAGTACGTACAAGTGCTGTATTTCAGTGTATTC

AAATGAGTTCAATTGAGGATGATGAAGATCAATTAGCATATCAAGCTGCTGTGAGCATTG

GTGGACATGTTTTCAAAGGAATTTTATATGATCAAGGTCATGAAAGTCAGTACAATAACA

TGGTTGCAGCCGGAGGCGATACGTCTTCCGGTGGTAGTGCTGGCGGAGTTCAGCACCA

CCACCATAATTCCGCTGCAGTAGCTACCGCCACCACTACAAGTGGTGGCGATGCTACTG

CAGCGGGTCCATCGAATTTTCTAGATCCTTCTTTATTTCCAGCTCCCCTTAGCACTTTTAT

GGTAGCTGGTACGCAATTTTTTCCACCTTCAAGATCTCCTTGA
```

An amino acid sequence of SEQ ID:2 of the transcription factor TF19(6):

```
MANFFSLGGNQEQQHQEISSSQALVPTESNNWFLYRNEHHHHHHNQEIPNTYKGFELWQS

GNTPQHQHQHHQQQQQFRHPIYPLQDLYSTDVGLGVGPSRSGFDISAGDHEASRSGFVM

MRSGGGGISCQDCGNQAKKDCQHMRCRTCCKSRGFQCQTHVKSTWVPAAKRRERQQQL

AALQQQQQGHNNNNNNHKNKRQREDPSASSLVSTRLPSNTNGLEVGKFPSKVRTSAVFQ

CIQMSSIEDDEDQLAYQAAVSIGGHVFKGILYDQGHESQYNNMVAAGGDTSSGGSAGGVQ

HHHHNSAAVATATTTSGGDATAAGPSNFLDPSLFPAPLSTFMVAGTQFFPPSRSP
```

A genomic nucleic acid sequence of SEQ ID NO: 3 encoding the transcription factor TF 19(6).

```
GCAAGTCAAATTGTATATGCTCTTAATTAGGGTTTATGCACCTAGAAGTAGTATTTTAATC

GCATATTAGTTATCGATGTTCCTAAATTAATCGCCTATTAGTTATCGATGTTCCTAAATAT

AATTGACCTAATTACAAAATTAAGATAGAACTGATTATATTTTTCAATTTTATCCTTACAA

GGAGCAATTCTTTTTGAAAGTATGAACCACTTTGTAAAGTTTTTTTTAAAAAAAATCTTAA

AGGAGTAAATCAGTAAAACTACCTTTCATATTTATGATTTTTTAAGAAGCATGTAAAGAAA

AAATAGAAAATCAATATAGAACGAAAAAAGAATTTTATAAAACCTCATAACTTAATAAAAA

GAATCATATTTATAAGAAATATTTTCTTCCCACATGGAATAATAAATTGCACAAACTGTAA

ATATTCTCTACTACAATATAATGTTATAACACACGTATACCGTTGGTTTTTCAGTATAAATA

TAATATCCATATTTTAGATATATTAGCTGTTAAAAACAATATAATATGGATGGAGACAAGT

TAAATGTATGTAATTTTACCTTGTAATCCCAATTCTCAATATATATATATATATATATATA

TATATATTCCTCCAAGACAAAACATTGGATTTTTATTCTAGGAACTTGAATTAAGAATTCA

ATTTACTCGTAAAAATTAAAAAGAAATTTCTTATGATCTTATCAAATATTTAATAGGTGAAT

AGTTAAATTTGACAAGTTAAATTAAGATGTATGTCCATCACCTCATCATAATTCAAATTATT

TTAACAAATATCCTTAATCATGATCTTCTTTCTTTTTAGGTTGAAATAATTATCATTAGATT

TGTACATAGTATAGGAATATATTAAGAGCTAATATATCTAAAATGTGGATAAATAAAACAA
```

```
-continued
TTCTTGCTCAAAATTTTAAATAGTTTTAATACTTTTACAATACTTGACACGCGGCATTATAT

AGCCAACAATTTTACGGGCTAAGACATAACATTTATCTTGGAAATTCTCTATTATTAATCA

TTAGCTTAGATTGTCTGAGTTTTTGAAGGTCTTTTATTTAGTTATAGGCAATTTTACCTAG

TTTTATAGAATTAAAATTATTGTCCGTTGTTATATTTAGGTAAGAAAAAAAGTTAATAAATC

AGACAAGAAAATATAAAGAACCGAAATAATTATGTAATGCCTAAAATAGTTGGTTTTATAT

ACATAAAGACTGTTGAAAATTGAAATTAATATTGCGGCTCCTTCATTTATTGGTATTACTG

TTAATTACGTGATTGAAAGGAAAAAAAAGTTTTACCAAAAAAAGTATAAAATAAGTTT

TGTACTTTATGTCAACAGTTAGTCATCAATAGTTACTGCTATAATACTAGGTGCCAACACT

ATGTATAATTCGAATGTGATAATAATTTCTGGAAAAAAAATTAAAGGATATTTGATTTGA

TATGGTCCTAGATAATGTAGATGATGAAGGGGTGTTAATTAGTCGTTTCAAATTGATAGG

TTATTTTGAAAAATTGTGTCATATTAATTGTTTATATTTTCAATGATGTATGATTAAAATTAA

AATTTTTGAATCTGTCTTAATCGTTTTGGTTTCTCTTTGATTTAGGTATAATTCAAATTGAT

GGTTAATTTTTTTAAACGTCATCTAACAACTATAAAATTTGATAAAAAATATTTAAAATTTA

CAATAACATAAAATGAAAATATGTTTTCCAACTATACCAATTTAGGAGGAGAAACATAGTT

ATTGTTTTACTATTATCGCTAGTATTATGAATGAGATATGAAAATTTATATTAATTTATATT

GGAATCTATAATTGATTTTATTAAAAAAAATTAAGTGCGTGTACTTTGACATTTTTTTGTT

TTTAACTCGGCATTCAAAGTTCATATTGAAGTTTTAACTAAATTCGAATCGCACTCTTCAG

AGCAATGCAGGGATGGGTCTCCCAACAACATTTTGTCGATAGTCTATACCCAGAGCTCG

AACTTAAGACCTCTGATTAAGAATAAAATACTTCATTTATAAACTGATCATCTTAATATTTT

CAAAATTTAAATGTCACATATTTTCTAAGATATCCTCGAAACATAATAATAAGTTGAAATG

TATAATGTTTGATTGAGACTAAACTGAGGCGTTTATATATACAATCGTAGAATTAAAATAT

TTAATTGCCATCTGAAAATTAATTTAAATATTTATCTATGTACTATACCTTAATTAATTCTTT

CATGACAAACTTTCTTGGACATTTTTTCATGAAAAATGCATATAACTTAAACAAGGCCGAT

ACCTTACACCCAAATTGGACAGTATATTTAGAAGAGGGGAATAATGGTAAAGAGGGCC

GGTATCAGGTTTACACAGAGATGAAAAGTTAGGTGGAGTTTATTTGTTCGGATGGATTTA

TCAGTTTTTTCGTAGATTTTATATTTATATTAGATTCTTTTTTTTACGTATATATTAAATTAT

AATCCCTAAACAAATTGATTTAGAATCTCAAACTCATAATCTTAACTTCGCCCCTAACTTT

TATATATATATATATATATATAATATTTTTAATATATCATTAGTTACACATTATTTTTTATATT

ATGTTGTGTATTACTGATGAATAATGATTTATGGAAATACAAAAAGCTCTTATTCAGTAAT

ACATACATTAGTATGATCATCTTTTTTCACATTCTTTCCATCGCGATATATGTTTTTTTTTT

AAACTATAACACAATAAACACTGCATTAAAAATAATTGTACATATTTTTTGTGTCTCAATTT

ATGTGATACCTTTTAGTTTTTTAAGAGCTAAACAATTTAAATTTGAGCGAGAATTTACGCA

TGAAATTTTCGAAAATTCTAAAAAGAAATTTATATATTAATAAAAACTACGTAAAAATACTA

TAAGACACAATAATTGACAATTCAAAATATTTAAAAGTCAAAGATATACTTATTTGAATTTC

AAAATCTGAAAAGTATCACATAAATAGGAGGAGAGAGTAACGAATATCAATATTAATGAT

ATATTATATTCACCACTAATATTCTTAAAAATAAATATTAAAAACACCATTAAATTCGATGT

GAATTATTAGTTTGATCCCTGAACTATTGACAGTATTATAAACACTCCTCTACTGGGTTAG

ATGAACTTAAATACACACTCGATCTTGTCACAATGATGAAATACACCCTAATGAAAATCAT

ATTTACTCTTCCTATTTCTAACCATCGGAAAGAGTCATCGTGGCTAGGAAACTATACTAG

CGACCTACCCAATTCATTATAGAAATTTTCGCGATCAATGATTGAAAATTTAGAATGTTTC

CAACACTTTATCTGTCAACTTTTTATTAAGAGTTTCAAGCTCGTATAAGAATTTGAAATCA
```

-continued

```
CTTTTAGTATATCATGTAGTAGATCTAAATATATTTAAAATTATTATAAATTTTTTTTAAAAA

ACTAATAATTCACACTAAATTGACAAATATCTTCAATACTTAGCTTCTCACTTATTTTATAC

GACCTACCAAACAATCGCGAAACTTTTTAAGTTACTGCAAACTGTAGCGGTAAAGAGAG

GGGAGGGGGGGGGGTAGTTGTGGTGCTTTTTAGCGTTGGCGGCGTTTGCAGAGCTG

TAATATATATAATATACCTTTTCTATTAATGTACCCTCACTCACTCACTTCCTCTCCATAAT

TCTTTATACAAACAATCATTTTTTCTTAAACTTGCTCTATTATAAATTCACATTTTTTCTTTA

TATATACACATACATATAGAGCAAAAAAGAAGTTCTAATTTTGTAAACCCTTCAAAAAAAA

GAAAAATAATTTTTTTTGAGATCATAAATGAAGAAATCCAAGGGATACAAACATCATATTT

GTGTTATAAGTTGGTGCACTTTTGTGGTATGGATTGTGATTAATCACTAATCATAATCAAG

ATTAACAACAAGTAATGGCTAATTTCTTTTCATTAGGTGGGAATCAAGAACAACAACATC

AAGAAATTAGCAGCAGCCAAGCATTAGTACCCACAGAGAGTAATAATTGGTTTTTGTACA

GAAATGAACATCATCATCATCATCATAATCAAGAAATACCCAACACTTACAAAGGTTTTGA

GTTATGGCAAAGTGGTAACACTCCACAACACCAACACCAACACCACCAACAACAACAAC

AGTTTCGTCATCCGATTTATCCTTTGCAAGATCTTTATTCCACTGATGTTGGATTAGGGG

TTGGGCCAAGCAGAAGTGGCTTTGATATATCTGCAGGTGATCATCAGAAACAGATTTAG

AATTTAAACTTTATCTATTCAGTACTTTCTAAAGTACTTATAGATCTATAATTTAAGTTTGA

TAAATTTAATATTTATGTTCTAAACAATTCACAACATTTTGCAATTAGGGATTTCGAAACGT

ATTTACTGAAGCATGTTAGAATTCCCAGCCTCGAAAAGGCATGGGAATTTGGTCTATGG

ACTTGGGAAATTCTCCATTCATGAGCTAACTTTTGAGGTTAAATTAGGTTCATATGTCATA

TCTTTACATGATATCAGAGTAAGATTCATCTCAATTCTTTGTTCACCAATATTGGCCCCCC

ATATTATTGTGTCCACAATCTAGTTAACCTACGCTGGCCCCTCCATATTACAGTGTCCAC

GTTCTAGTTAACGAGATCTGGGCTTGCAGAAGAGTGTAAAGAATTCAGAAAAAGGATGA

GTATTTGGTCTCCTTGTATAAACTTGAGCAATCCTTCCTTCATGAGCTAGCTAGTTTTGG

AATTAAGTTAGACTAGATGTCATATCTTTTAATATTTATGTTCTCACTGTAGAACCATATA

GCAACGAAACTATAGTACTATTTGTTGCACCGCTCTCTCTATATATATCGTGCATATTAAG

TTCAATTGAATCTGTTGCTAAAAGGCGGGATGGGGATTATTATTGTGCAGGTGATCATGA

GGCGTCGAGGTCGGGATTCGTGATGATGAGGAGTGGTGGAGGAGGAATAAGTTGCCA

AGATTGTGGGAACCAAGCTAAGAAAGATTGTCAACATATGAGGTGTAGGACTTGTTGTA

AGAGTAGAGGGTTTCAGTGTCAAACTCATGTGAAAAGTACTTGGGTTCCAGCAGCTAAA

AGGAGAGAAAGGCAACAACAACTTGCTGCTTTGCAACAACAACAACAAGGACATAATAA

TAATAATAATAATCATAAGAATAAAAGGCAAAGGGAGGATCCAAGTGCTTCTTCTCTTGT

GTCTACTCGTTTGCCTTCAAACACTAATGGTAAAGTACTTCATGTTTTTCTTACCTTTTCA

TTGCTACGTCTGTTTTAATTTAAAGGTCTTAGTTTGACTGAACATGAATATAAGATGTTGA

AATTGAAAACGTAGATAAATATTTAAATTGAAACGAGGGAATAATATTAATTTTTTTTGTA

TCACACAAAGACATAGAGTCTTGAGATCCATCATGTAAAGAAGATTAATTTGATCATTGC

CTAAATGAATTCTATATAAAGTAAGTCTATAGAGAAAAGAGACCCTATAGTAAATTCGTCA

GCTTTTTCTTTTCTATTTGTCATTCTCTTCTTCCATCATCACTCTTCTTTTTTATTACTCTA

CAAAAGATTGACAAAAATTCGTAATGAGATATATTCAAATTTTTGAGTTAATTATGAATTTT

TAATTCTAGTTAATAGAAAGTGTGAATAAATTATTTATATGTATTACTAACAAAATAGCAAA

ACTAAAACTTTACTTGTACCCTTGCGCGTGTGTATGCACAATTTCTTTCTCTTAGACCTAC
```

-continued

```
ACATGATATTTATCTCGACCCTAAAAAGATCACCATTATTCTTAATTTCAATTTTCGTCAAT

TTTTTTTAAGATAATAACTATTATTTGAGTAATAATATATGTGACTTACCCAAAAAACTGT

TAGTGGAGTGAGTATTTGAGAAACCAACTCTCTAATTCATGTATAATAATTGGTGTTATCA

TATATTGTCATTAGTATTGGAATTAACTTATATATCTATTAGTAAATGTACTTTTGAAATAA

TAACTATTATTTGAGTAATAATATATGTTGCTTACCAAAAAAATAACTATTAGTTGAGTGG

CTATTAACTCTCCAAATATGTATAATAATTGGTGTTATCATTTTCATTAGTATTGGAATTAA

CTTATATATAGTAAATGCACTTGCATTTCAAATTTTTTACCTGCTTTTCCTTTTAGTTC

GATTAAAATAAATTGACTATTTTTCAAGCAAGTGTTTATTCTAAACTTTTCAGATGAAATGT

TTAAAAAAACCACAAGATTAAATAGTGTTTTGATACATTTGACATATTTTTAGTTTTAGACC

ATAAAATTCAAATTGCTTTACTAAATTTCGTGTCAAGTGATACTAGGTAAAAAAAAATATT

TATTTGCAATACATTAGTCCAAATAAACCTAATTTTGTATTATGGAATTTCATGTGTTATTT

TTAGGGTTAGAAGTGGGAAAATTTCCATCAAAAGTACGTAAAGTGCTGTATTTCAGTGTA

TTCAAATGAGTTCAATTGAGGATGATGAAGATCAATTAGCATATCAAGCTGCTGTGAGCA

TTGGTGGACATGTTTTCAAAGGAATTTTATATGATCAAGGTCATGAAAGTCAGTACAATA

ACATGGTTGCAGCCGGAGGCGATACGTCTTCCGGTGGTAGTGCTGGCGGAGTTCAGCA

CCACCACCATAATTCCGCTGCAGTAGCTACCGCCACCACTACAAGTGGTGGCGATGCTA

CTGCAGCGGGTCCATCGAATTTTCTAGATCCTTCTTTATTTCCAGCTCCCCTTAGCACTT

TTATGGTAGCTGGTACGCAATTTTTTCCACCTTCAAGATCTCCTTGATCGTCCACATTGAT

AATATTGAGGTGTCTTTTTAATTTTTATGTCAAGAGATTTGTTTTTAATTGAAGTATTGATG

TTGAATTGAGTTGTTTACATTAATTCTCTTTGGATTCTACATGAAGTTGTTTTTTTTCTCT

AGTTCCTTATGGTTAATTATTGGTATCATATAGATTTGCTTTTTTATTTCACGTTAAGATGA

TAATATAAGATAAGATGATAATATACTTAAATGTATATATGTTTTGGGTTGAGTCTTACGA

TTACTTATTATTAGAATTTTTTGTATGTGTATTCGGCTCATAATGTGCCAAAAGATAACAA

AAGCAAAATTTAAGAGCATTCACATAATATTATAAGTTTGTGATGGACTGTAAGTATATTT

TAGATTTTTTAATTAGAGTTTTTAAATTTAAACCTAAAAGAAATCGTATTTAAAAAGAGCAG

TTTACCCTATAAGTGATTTTTTTAAGAATAAATATGGATTAGTCGAACCCAATAGTCGGGC

AACAGTTAGAAGCTAAAAAAGATTATAATTTTAAGAAAATACTTACTTTATAAAATTGAGA

TATTTGGTTAAGTTTTTAGAGGGGGAAAAGAAATGTGCTTTTGAATAATAGCATGAATTA

ATCTTTACAATTAGAAAAAAGAAAATTAAAAATACAAAAAGTAATTGTGAAATTAGGTCA

AGCACAAACTAAGGTTCTAAAACTGATTTTAAAAAAAAACTTTTAAATTAATTAATCAACA

CAAAATTATTACTCTCCAAAAATATTTTCTACATAATACTTATCAAAATAAATATATTTAGA

AAATTTGGCCAAACTAACATGACTCTTCTTGATTAAGCACATAAATCAAGTTGTTAATAAA

ACTTTGGCTTTATAGCAATGACTCATTTGCTTTCAAAACATAAAAAAATGAACAAACATTA

AATATATATTTAACGGAGTAAGATATATTCCAAACTAGGACACTAGAAATGGTGAAAGCT

TAGTACGTTTGGAACATCAATTCAATTAAACTCGAATGTCACTGTTTAACTTGTCTTAATA

TATGTGATAATATTTGATGGATCTTAAATATTATTTCTTTAAAAAATAATTATTCGTTAGAA

GGACAATAAGTGCTACAATGACTTAAATTTCTAAATTTTCAACTAGGCATAATCCTTCAAA

ATAACTTTCATCATACTTTTGAATAATTAAATATGATATTATTGAAGTTATGTAAATTTTCAT

GTTTCGGGCTTGTTCGGGTTTTTTAAATATCAAATCAAATTATTCGTGTAAAATTTTTAAA

ATTATAAATCAGACCAAATTAATAAAATTCAGATTTTTTCGGGGTTTTCAACTCTGGGTTG

ATTCGTATTTTTCAAGTACCAAACCAAACCATTGTGTCGAATTTTTAAATTTTTAATCAAAC
```

```
-continued
CAAACTAATAAACTTCGGATTTTTCCAGATTTTTAGATTTTTCGGGTAAAGTTTGCATACA

AACATATAATTAACTTGTGCTCCAAATATTTCTTTAGTCCAACCATAATATAATTATCTAAG

GTATTTCTTGAAAAAATTACACAAAAGATGAGATGAGTATTGATGACACAAAAATATTCAA

TAAAAAATAACAATAAATCATCATATAAAATAAATATTGTAAAGTCATAATGAAAATAATCA

TAATTTAAAATTTTTAAATCATGCTAAAATAAGTTTAATAAGTATTAGTTACATTATTAAATA

TTTAAGGAAAACAAAAATTAGATTATGTAAATAAATATAAAACTAAAGAACAAATATTCAA

TATTATTGTCATTTTTAGTGTTGAATTGATTTTTCTTTTTGCATTAGTATTAATTTAATTTT

AATTTAAGCTTTATTATAATTATCAATCTATGAACTATAATCTATATTGGACCATTCCAAAT

TCTATATTTTAAACTTGAAACAATATATTAAAAGTTAAAAACTATGAAATAGTATAAGAAAT

ATTTTAAAATAATATCAACGTAAATATTTTATGTATAAAATAATATTTTACACATATAATATA

AGGATTTTTTCCCGATTTGATTCAATT
```

EXAMPLES

Example 1

Plant Material, Hormone Treatment and RNA Isolation

Tomato plants (Solanum lycopersicum cultivar Moneymaker) were grown in soil in a greenhouse with day/night temperatures of 23° C. to 18° C. and a 16/8 hours light/dark regime for 4 weeks. Trichomes were collected at the bottom of a 50 ml tube by vortexing stem pieces frozen in liquid nitrogen. The remaining cleaned stem segments were thoroughly brushed to remove all remaining trichome material (bald stem sample). Whole stems (including trichomes) and leaves were also frozen in liquid nitrogen, the material was ground and total RNA was isolated using TRIzol® (monophasic solution of phenol and guanidinium isothiocyanate) (Invitrogen, Paisley, UK).

Jasmonic acid (JA) was applied to plants by spraying 1 mM solution made with tap water containing 0.05% SilwetL-77. Control plants were sprayed with tap water containing 0.05% SilwetL-77. Trichomes were collected 24 hours later and total RNA was isolated as described above. DNA was removed with DNase (Ambion, Huntingdon, UK) according to the manufacturer and cDNA was synthesized from 1.5 µg RNA using M-MuLV Reverse Transcriptase (Fermentas, St. Leon-Rot, Germany) according to the manufacturer in 20 µl volume that was diluted to 50 µl prior to using it for PCR.

Example 2

Constructs and Stable Plant Transformations

The full SlTPS5 promoter and a series of 5' deletions of it were generated using PCR. A SacI restriction enzyme site was created at the 5' end of each forward primer and an XbaI restriction enzyme site at the 3' end of the reverse primer. Fifty ng of plasmid DNA pKG1662adp-SlMTS1p:GUS were used as template with 0.25 units of Phusion Hot Start polymerase (Finnzymes, Espoo, Finland), each primer in a concentration of 0.4 mM and dNTPs in a concentration of 0.2 mM in 25 µl reaction volume. MgCl$_2$ was added to the PCR mix with a final concentration of 0.3 mM. The cycling program was set to 1 min 98° C., 30 cycles of 10 sec 98° C., 30 sec 58° C., 60 sec at 72° C., followed by 5 min final extension at 72° C. and cooling to 12° C. until removed from the thermocycler.

Primers used (5'->3' sequence, numbers indicate the position of the 5' nucleotide of each primer. The A of the start codon ATG is assigned to +1):

```
Sl_TPS5p-18 R
                                            (SEQ ID NO: 4)
GCTCTAGATTTATTTGTTCTGCTCAA

Sl_TPS5p-1253 F2
                                            (SEQ ID NO: 5)
CGAGCTCGTTTCATTCAAAGTAGTGG

Sl_TPS5p-1045 F
                                            (SEQ ID NO: 6)
CGAGCTCAGCTGAACCAAATCCCAA

Sl_TPS5p-805 F2
                                            (SEQ ID NO: 7)
CGAGCTCGTCCTATTTTTCCATATTG

Sl_TPS5p-612 F2
                                            (SEQ ID NO: 8)
CGAGCTCATCAACAGTATTAAATGTGCTTC

Sl_TPS5p-408 F2
                                            (SEQ ID NO: 9)
CGAGCTCAGTAATAATGAAAATCGCATCG

Sl_TPS5p-207 F2
                                            (SEQ ID NO: 10)
CGAGCTCACATGTGCTATTTTTATGCTA
```

The 6 PCR products were purified using an Invitek (Palm Springs, Calif., USA) column according to the manufacturer's protocol. They were subsequently double digested with SacI and XbaI and ligated upstream of the ATG start codon of β-glucuronidase fused to yellow fluorescent protein (sYFP1) in the SacI and XbaI sites of the vector pJVII, replacing CaMV 35S promoter (FIG. 1). The PCR products were verified by sequencing and the expression cassettes (promoter fragment+GUSsYFP1+NOS terminator) were transferred to the binary vector pBINplus (van Engelen et al., 1995 Transgenic Res 4: 288-290) by digesting with restriction enzymes SacI and SmaI and ligating in the multiple cloning site of pBINplus at the same restriction sites. These 6 constructs and an empty pBINplus vector were introduced to Agrobacterium tumefaciens strain EHA105 and used to create transgenic plants using explants derived from cotyledons of sterile seedlings of Solanum lycopersicum cultivar Moneymaker (MM), as previously reported (Cortina and Culianez-Macia, 2004, Plant Cell Tissue and Organ Culture 76: 269-275).

Example 3

Analysis of Transgenic Plants

One transgenic line was obtained from the empty pBINplus vector, four independent transgenic lines from the full length SlTPS5 promoter construct, three from the 1045 bp SlTPS5 promoter construct, five for the 805 bp and 612 bp SlTPS5 promoter constructs, eight for the 408 bp SlTPS5 promoter construct and nine for the 207 bp SlTPS5 promoter construct. Insertion of the transgene was verified by PCR on genomic DNA isolated from leaves of the different T0 lines.

Primers used (5'->3' sequence):

```
pJVII_1182GUS_R
                              (SEQ ID NO: 11)
CCACCAACGCTGATCAATTC pJVII_6936_F
                              (SEQ ID NO: 12)
ATGTGCTGCAAGGCGATTAAG
```

The PCR was performed with Taq DNA Polymerase (Fermentas, St. Leon-Rot, Germany) in 25 µl volume according to the manufacturer and the cycling program used was set to 2 min 95° C., 30 cycles of 30 sec 95° C., 30 sec 58° C., 90 sec at 72° C., followed by 5 min final extension at 72° C. and cooling to 12° C. until removed from the thermocycler.

Figure 2:
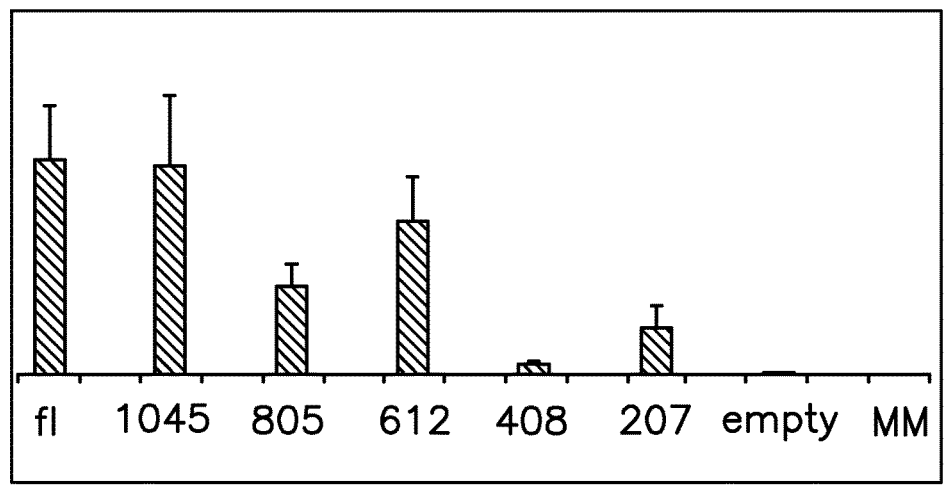
FIG. 2 is a set of bar graphs showing quantification of GUS expression in isolated trichomes from stems of transgenic 5' SlTPS5 promoter deletion plants and controls. Average relative GUS activity for each promoter construct (full length (fl), 1045 bp, 805 bp, 612 bp, 408 bp, 207 bp), empty vector control and untransformed Moneymaker plant. Trichome-specific activity is lost at 408 bp and then partially restored at 207 bp. The 207 bp fragment was chosen for the Y1H assay.

Initial YFP expression of the T0 plants was estimated under a fluorescence stereoscope and it was determined to be specific for the "head" of the type VI trichomes of the plants (data not shown). Trichomes were isolated from T1 plants as mentioned above, crude extracts were prepared according to Jefferson R. A. et al., 1987, EMBO J 6: 3901-3907 and the enzymatic GUS activity was determined spectrophotometrically using 4-methylumbelliferyl β-D-glucuronide (MUG) as a substrate (FIG. 2).

Example 4

Yeast One Hybrid and Identification of Clone 19(6)

The 207 bp SlTPS5 promoter fragment showed trichome specific activity, although less strong than that of the full length promoter (FIG. 2), and therefore this fragment was used for the yeast one hybrid (Y1H) assay.

An EcoRI restriction enzyme site was created at the 5' end of the forward primer and the reverse primer Sl_TPS5p-18 R with an XbaI restriction enzyme site at the 3' end were used in a PCR to generate the 207 bp fragment for cloning. PCR was performed with Phusion Hot Start polymerase (Finnzymes, Espoo, Finland) as mentioned above, except extension time was 30 sec at 72° C.

Primer used (5'->3' sequence):

```
Sl_TPS5pEcoRI_207F
                              (SEQ ID NO: 13)
CGGAATTCACATGTGCTATTTTTATGCTA
```

The PCR fragment was purified using a Roche (Almere, Netherlands) column according to the manufacturer's protocol. Then it was double digested with EcoRI and XbaI and ligated in the multiple cloning site of pHISi vector (Clontech, Mountain View, Calif., USA) at the same sites. After verifying the sequence, the construct was integrated in the yeast pj69-4a genome according to the Clontech MATCHMAKER One-Hybrid System manual. A cDNA library created with mRNA from Solanum lycopersicum cultivar Moneymaker trichomes was screened 3 times according to the manufacturer's protocol (Clontech, Mountain View, Calif., USA). Three Y1H screens yielded 76 clones, among which one putative transcription factor 19(6), appearing 32 times. The clone was sequenced using primers that fit on the library vector (pAD-GAL4-2.1, Stratagene, Santa Clara, Calif., USA) and specific primers designed on the obtained sequence to get the full length clone.

Primers used (5'->3' sequence):

```
pActF
                              (SEQ ID NO: 14)
TAATACCACTACAATGGATG pAct_seqR
                              (SEQ ID NO: 15)
CAACTGTGCATCGTGCAC 19(6)_seqF
                              (SEQ ID NO: 16)
TTATGGCAAAGTGGTAACA 19(6)_seqF2
                              (SEQ ID NO: 17)
TCAGTGTCAAACTCATGTG 19(6)_seqF3
                              (SEQ ID NO: 18)
AAGTACGTACAAGTGCTG
```

Figure 3:
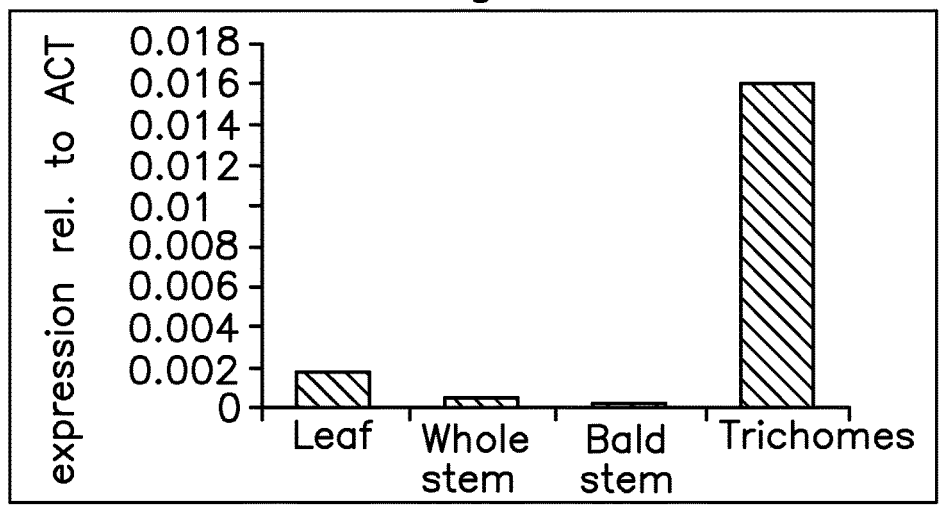
FIG. 3 is set of bar graphs showing results of Quantitative Real Time PCR for a candidate gene 19(6).
Figure 3:
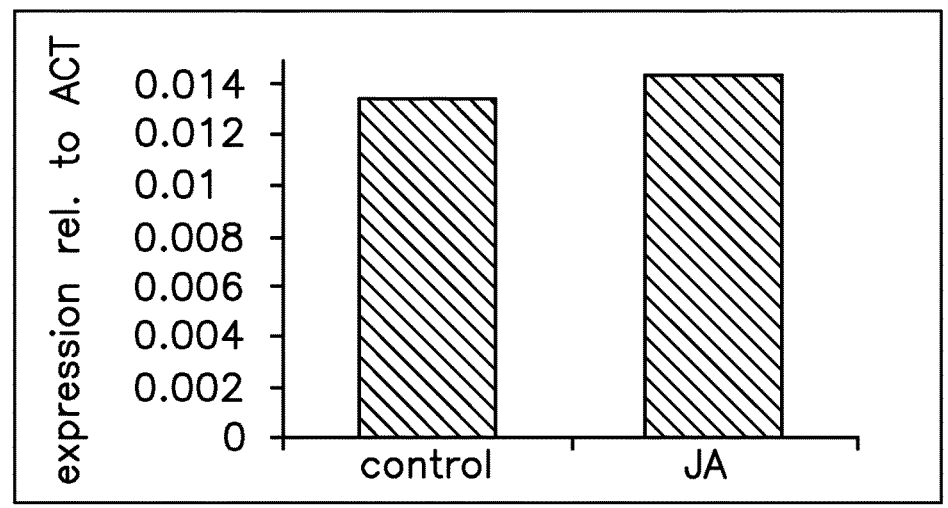

The candidate transcription factor was checked for JA-inducibility and trichome specificity by quantitative real-time PCR (FIG. 3). The different tissue- and control and JA treated trichome-cDNA was obtained as described above.

Example 5

Real Time Quantitative PCR

RT-Q-PCRs were performed in the ABI 7500 Real Time PCR System (Applied Biosystems, Carlsbad, Calif., USA) using the Platinum SYBR Green qPCR SuperMix-UDG kit (Invitrogen, Paisley, UK). Each 20 µl reaction contained 0.25 µM of each primer, 0.1 µl ROX reference dye and 1 µl template cDNA. The cycling program was set to 2 min 50° C., 7 min 95° C., 45 cycles of 15 sec at 95° C. and 1 min at 60° C. and a melting curve analysis. Primer pairs were tested for specificity and for linearity with a standard cDNA dilution curve. The tomato Actin gene (ACT) was used as constitutively expressed control gene.

Primers used (5'->3' sequence):

```
ACT_QF
                              (SEQ ID NO: 19)
TTAGCACCTTCCAGCAGATGT

ACT_QR2
                              (SEQ ID NO: 20)
AACAGACAGGACACTCGCACT

19(6)_QF
                              (SEQ ID NO: 21)
TACAAGTGGTGGCGATGCTAC
```

-continued

19(6)_QR
(SEQ ID NO: 22)
ACCTCAATATTATCAATGTGGACAATC

Example 6

Transactivation Assay

DNA binding activity was confirmed in transactivation assays. A NcoI restriction enzyme site was created at the 5' end of a forward primer and a SacI restriction enzyme site at the 3' end of a reverse primer and a full length cDNA 19(6) was generated in a PCR performed with Phusion Hot Start polymerase (Finnzymes, Espoo, Finland) as mentioned above. Fifty ng of plasmid DNA pAD-GAL4-2.1_clone 19(6) were used as template.

Primers used (5'->3' sequence):

Ncol_19(6)F
(SEQ ID NO: 23)
catgccATGGCTAATTTCTTTTCATTAGG

SacI_19(6)R
(SEQ ID NO: 24)
cgagctcTCAAGGAGATCTTGAAGGTG

The PCR fragment was purified using a Roche (Almere, Netherlands) column according to the manufacturer's protocol. Then it was double digested with NcoI and SacI and ligated downstream of 35S promoter in the same sites of the vector pKG1662-35S:GUS, replacing β-glucuronidase. The PCR product was verified by sequencing and the expression cassette which included 35S promoter, transcription factor 19(6) and nos terminator, was transferred to the binary vector pBINplus (van Engelen et al., 1995 Transgenic Res 4: 288-290) by digesting with restriction enzymes HindIII and EheI and ligating in the multiple cloning sites of pBINplus digested with HindIII and SmaI. The construct was introduced to *Agrobacterium tumefaciens* strain GV3101.

Five week old *Nicotiana benthamiana* leaves were co-infiltrated with *A. tumefaciens* GV3101 cultures carrying various promoter:GUS reporter and the 35S:19(6) effector constructs. Specifically, the promoter constructs used were pBINplus-ShMKS1p:GUS, pBINplus-SITPS11p:GUS and pBINplus-SITPS5p:GUS. These constructs were made by cloning into a PJVII-GUSSYFP1 vector each of SITPS5, SITPS11 or *Solanum habrochaites* methylketone synthase 1 (ShMkS1; Fridman et al., 2005 Plant Cell 17:1252-1267, published on line Mar. 16, 20005) promoter sequences between SacI and XbaI sites, and nucleic acid sequences encoding β-glucuronidase (GUS) fused to a yellow fluorescent protein (sYFP1) between XbaI and BamHI sites (Schematic drawing of PJVII-GUSSYFP1 is shown in FIG. 1). A control pGreen-35S:RFP effector construct was also used (pGreen; Hellens et al., 2000, Plant Molecular Biology 42: 819-832). In order to correct for infiltration errors *A. tumefaciens* GV3101 culture carrying pBINplus-35S:LUC was also added in each culture mix in a ratio of 5 (promoter: GUS): 5(35S:TF): 1(35S:LUC). Two days later leaf disks from the infiltrated areas were collected, frozen in liquid nitrogen and crude extracts were prepared in extraction buffer containing 25 mM Tris phosphate pH 7.8, 2 mM DTT, 2 mM CDTA pH 7.8, 10% glycerol and 1% Triton X-100. The enzymatic GUS activity was determined spectrophotometrically using 4-methylumbelliferyl β-D-glucuronide (MUG) as a substrate according to Jefferson R. A. et al., 1987, EMBO J 6: 3901-3907. The luciferase assay was performed using the same extraction buffer according to van Leeuwen et al., 2000, Plant Molecular Biology Reporter 18: 143a-143t. Enzymatic GUS activity was normalized for luciferase activity for each sample and results are presented in FIG. 4.

Figure 4:
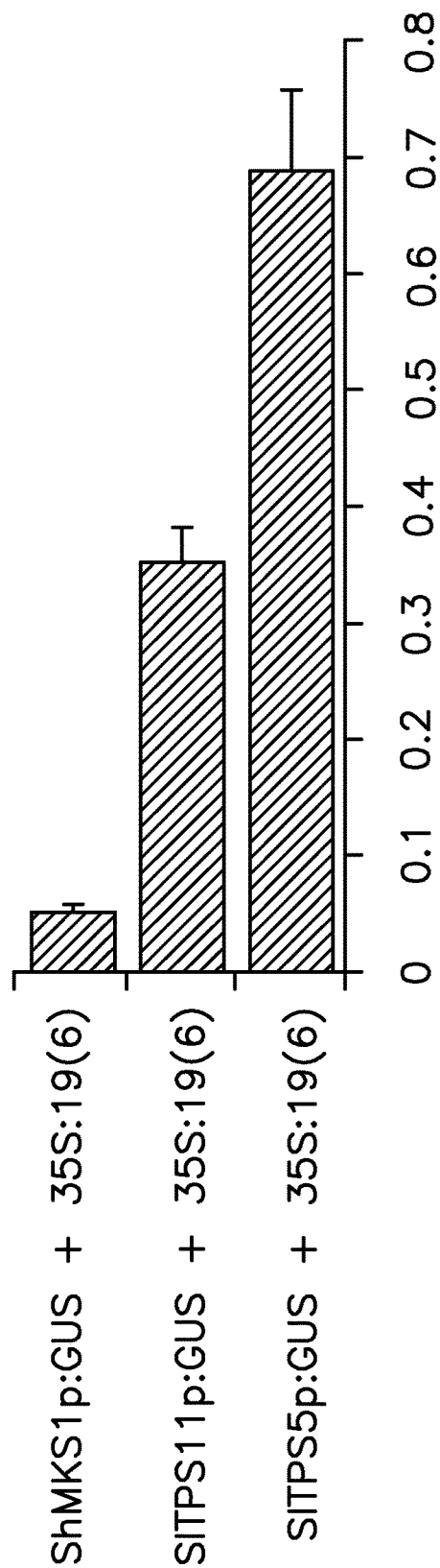
FIG. 4 is set of bar graphs showing average relative GUS activity in *N. benthamiana* plants. Five week old *N. benthamiana* leaves were co-infiltrated with *A. tumefaciens* GV3101 cultures carrying various promoter:GUS reporter and the 35S:19(6) effector construct. Average relative GUS activity normalized for 35S:luciferase activity is shown. Activities of these promoter:GUS reporter constructs in *N. benthamiana* with a control 35S:RFP effector construct were approximately 0.05. Enzymatic GUS activity of the crude extract was determined spectrophotometrically using 4-methylumbelliferyl β-D-glucuronide (MUG) as a substrate.

As shown in FIG. 4, the 35S:19(6) effector construct activated GUS activity in pBINplus-SITPS5p:GUS more than 10-fold over the control pBINplus-ShMKS1p:GUS construct. Additionally, the effector construct was also able to activate GUS in pBINplus-SITPS11p:GUS 7-fold over the control.

These data confirmed TF 19(6) capability to activate SITPS5 and SITPS11 promoters and shows that TF19(6) may be used in regulating expression levels of the TPS5 and TPS11, and alter terpene content in a plant, tissue or cell.

Example 7

TF 19(6) Sequence Identity

Polypeptide sequence identity was determined using BLAST® (Basic Local Alignment Search Tool) algorithm described in Althsul et al. 1990 J Mol Biol 215:403-410. BLAST® (Basic Local Alignment Search Tool) program is publicly available through the National Center for Biotechnology Information (NCBI) at the web site of the National Institute of Health, USA.

A BLAST® (Basic Local Alignment Search Tool) homology search identified that amino acid sequence of TF 19(6) has 40.68% identity over the length of the entire protein as compared to the Lateral Root Primordium (LRP1) protein, a member of *Arabidopsis thaliana* SRS (short internode related sequences)-type transcription factors with zinc finger motifs that are induced by auxins. Two zinc finger-type domains were found within TF 19(6): a zinc finger domain (amino acids 128-170) in the N-terminal part and a small conserved LRP1-type domain in the C terminus (amino acids 224-272). The polypeptide of the invention also possess conserved DUF702 domain of unknown function characteristic of SRS-type transcription factors. The BLAST® (Basic Local Alignment Search Tool) search also identified a tomato gene encoding a protein 45% homologous to TF 19(6) and containing one zinc finger-type domains and DUF702 domain. The function of this protein is unknown.

Example 8

Insect Bioassays

Insect bioassays are performed under controlled conditions in the greenhouse. Plants are modified using the methods of the present invention. For example: *Solanum lycopersicum* is modified by means of *Agrobacterium*-mediated transformation with pBIN 35S-19(6) (encoding the protein having the amino acid sequence of SEQ ID NO:2).

Alternatively, *Solanum lycopersicum* mutants are identified within a mutagenized population so that the mutants carry a mutation or mutations in a nucleic acid sequence of SEQ ID NO: 1 or fragments thereof encoding the transcription factor of the present invention. Insect pest resistance of modified plants is compared to that of non-modified control plants in choice- and no-choice tests as described in Bleeker et al., 2011 Phytochemistry 72: 8-73; and patent application WO 2010/099,985. Resistance to the following insect classes is determined: Lepidoptera; Coleoptera; Diptera; Hemiptera; Acari; Thysanoptera.

37

Insect Preference Test.

A choice test is performed in which insects at different life stages, e.g., larvae or adults, are allowed to choose between plants that produce terpenes such as linalool or nerolidol (through expression of a nucleic acid sequence encoding the amino acid sequence of SEQ ID NO:2) and control plants. The test determines the repellent activity of the terpenes produced because of the activating effect of the protein of SEQ ID NO:2

38

Insect Performance Test (No-Choice Test).

A no-choice test is performed to determine the toxic effects of the terpenes produced by activating expression of a nucleic acid sequence encoding the amino acid sequence of SEQ ID NO:2. In these experiments, insect pest species are forced to eat from (transgenic) plants that have modified terpenes production through expression of a nucleic acid sequence encoding the amino acid sequence of SEQ ID NO:2 and control (or empty vector) plants. Subsequently, insect performance, e.g., growth, development or fitness, is determined as a measure of toxicity.

The invention claimed is:

1. A method for increasing production of at least one terpene in a plant of the Solanaceae family, the method comprising transgenically modifying the plant to have an increased copy number of a nucleic acid sequence encoding a polypeptide having at least 95% identity to the amino acid sequence of SEQ ID NO:2 over the entire length, compared to a non-modified plant of the same genetic background, thereby increasing the production of the at least one terpene in the modified plant compared to the non-modified plant of the same genetic background.

2. A method for increasing production of at least one terpene in a plant of the Solanaceae family, the method comprising:
(a) contacting a plant cell from a plant of the Solanaceae family with a composition comprising a vector comprising a nucleic acid sequence encoding a polypeptide having at least 95% identity to the amino acid sequence of SEQ ID NO:2 over the entire length;
(b) selecting the plant cell transformed with the vector, wherein the plant cell overexpresses the nucleic acid sequence, wherein overexpression results in an increased level of the at least one terpene in the cell compared to a non-transformed plant cell; and (c) regenerating the plant from the transformed cell of (b), wherein the plant has the increased level of the at least one terpene compared to a non-transformed plant of the same genetic background.

3. A method for increasing production of at least one terpene in a population of plants of the Solanaceae family, the method comprising: (a) modifying a plant of the Solanaceae family to have an increased copy number of a nucleic acid sequence encoding a polypeptide having at least 95% identity to the amino acid sequence of SEQ ID NO:2 over the entire length, compared to a non-modified plant of the same genetic background, and (b) selectively breeding the plant to produce the population having the increased level of the at least one terpene compared to the non-modified plant of the same genetic background.

4. The method according to claim 1 wherein the terpene comprises at least one of a monoterpene and a sesquiterpene that repel insects.

5. The method according to claim 4 wherein the monoterpene comprises at least one compound selected from the group consisting of: linalool, β-myrcene, para-cymene, γ-terpinene, α-terpinene, and α-phellandrene.

6. The method according to claim 4 wherein the sesquiterpene comprises at least one compound selected from the group consisting of: neralidol, germacrene, R-curcumine, S-curcumine and 7-epizingiberene.

7. The method according to claim 1 wherein the terpene comprises at least one of a monoterpene and a sesquiterpene that attract insects.

8. The method according to claim 7 wherein the monoterpene comprises at least one compound selected from the group consisting of: β-phellandrene, limonene and 2-carene.

9. The method according to claim 7 wherein the sesquiterpene comprises at least β-caryophyllene.

10. The method according to claim 4 wherein the insects comprise sap-sucking insects and blood-sucking insects.

11. The method according to claim 10 wherein the sap-sucking insects comprise psyllids, whiteflies, aphids, mealybugs, plant hoppers and scale insects.

12. The method according to claim 11, wherein the sap-sucking insects further comprise thrips, mites and leaf hoppers.

13. The method according to claim 10 wherein the blood sucking insects comprise mosquito, ticks and midges.

14. The method according to claim 1 wherein the plant of the Solanaceae family is at least one crop plant selected from the group consisting of: tomato, pepper, eggplant, and potatoes.

* * * * *